United States Patent
Porco et al.

(10) Patent No.: US 10,981,850 B2
(45) Date of Patent: Apr. 20, 2021

(54) ONE-STEP FLOW-MEDIATED SYNTHESIS OF CANNABIDIOL (CBD) AND DERIVATIVES

(71) Applicant: TRUSTEES OF BOSTON UNIVERSITY, Boston, MA (US)

(72) Inventors: John A. Porco, Brookline, MA (US); Aaron B. Beeler, Cambridge, MA (US); Lauren E. Brown, Brighton, MA (US); Richard V. Trilles, Watertown, MA (US)

(73) Assignee: TRUSTEES OF BOSTON UNIVERSITY, Boston, MA (US)

(*) Notice: Subject to any disclaimer, the term of this patent is extended or adjusted under 35 U.S.C. 154(b) by 0 days.

(21) Appl. No.: 16/848,215

(22) Filed: Apr. 14, 2020

(65) Prior Publication Data

US 2020/0325091 A1  Oct. 15, 2020

Related U.S. Application Data

(60) Provisional application No. 62/834,036, filed on Apr. 15, 2019.

(51) Int. Cl.
*C07C 37/20* (2006.01)
*B01J 8/00* (2006.01)
*B01J 8/02* (2006.01)

(52) U.S. Cl.
CPC .............. *C07C 37/20* (2013.01); *B01J 8/001* (2013.01); *B01J 8/0278* (2013.01); *B01J 8/0285* (2013.01); *B01J 2208/00017* (2013.01); *B01J 2208/00539* (2013.01); *B01J 2208/00893* (2013.01)

(58) Field of Classification Search
CPC ......... C07C 37/20; B01J 8/001; B01J 8/0278; B01J 8/0285
See application file for complete search history.

(56) References Cited

U.S. PATENT DOCUMENTS

| | | | |
|---|---|---|---|
| 9,587,212 B2 | 3/2017 | Winnicki et al. |
| 10,059,683 B2 | 8/2018 | Dialer et al. |
| 2006/0194761 A1 | 8/2006 | Gu |
| 2010/0298579 A1 | 11/2010 | Steup et al. |
| 2016/0002195 A1 | 1/2016 | Makriyannis et al. |
| 2018/0244642 A1 | 8/2018 | Koch et al. |
| 2019/0023680 A1 | 1/2019 | Leahy et al. |

FOREIGN PATENT DOCUMENTS

| | | |
|---|---|---|
| WO | 2004092101 A2 | 10/2004 |
| WO | 2015032519 A1 | 3/2015 |
| WO | 2016135308 A1 | 9/2016 |
| WO | 2018200864 A1 | 11/2018 |
| WO | 2020099283 A1 | 5/2020 |

OTHER PUBLICATIONS

Ligresti et al., "From Phytocannabinoids to Cannabinoid Receptors and Endocannabinoids: Pleiotropic Physiological and Pathological Roles Through Complex Pharmacology", Physiol Rev., 96, (4.),1593-659, (2016).
Sekar et al., "Epidiolex as adjunct therapy for treatment of refractory epilepsy: a comprehensive review with a focus on adverse effects", F1000Res. 8. PMCID: PMC6396837 (2019).
Choi et al., "NMR assignments of the major cannabinoids and cannabiflavonoids isolated from flowers of Cannabis sativa", Phytochem Anal., 15, (6.), 345-354, (2004).
Citti et al., "A novel phytocannabinoid isolated from *Cannabis sativa* L. with an in vivo cannabimimetic activity higher than Δ9-tetrahydrocannabinol: Δ9-Tetrahydrocannabiphoro", Nature Scientific Reports, 9, 20335, (2019).
Von Widdem et al., "Abnormal Cannabidiol Affects Production of Pro-Inflammatory Mediators and Astrocyte Wound Closure in Primary Astrocytic-Microglial Cocultures", Molecules, 25,(3.), 496, (2020).
Tomko et al.,"Antitumor Activity of Abnormal Cannabidiol and Its Analog O-1602 in Taxol-Resistant Preclinical Models of Breast Cancer", Front. Pharmacol., (2019).
Hanus et al., "Phytocannabinoids: a unified critical inventory", Nat. Prod. Rep., 33, 1357-1392, (2016).
Mascal et al., "Synthetic, non-intoxicating 8,9-dihydrocannabidiol for the mitigation of seizures", Sci Rep., 9, (1.), 7778, (2019).
Ran et al., "Beta-Cyclodextrin-Propyl Sulfonic Acid Catalysed One-Pot Synthesis of 1,2,4,5-Tetrasubstituted Imidazoles as Local Anesthetic Agents", Molecules, 20, (11.),c20286-20296, (2015).
Shevyrin et al., "Cannabinoids: structures, effects, and classification", Russian Chemical Bulletin International Edition, 64, (6.), 1249-1266, (2015).
Russo et al., "Taming THC: potential cannabis synergy and phytocannabinoid-terpenoid entourage effects" British Journal of Pharmacology, 163, 1344-1364, (2011).
An et al., "Calix(8)arene Sulfonic Acid Catalyzed Three-Component Reaction for Convenient Synthesis of 3,4-Dihydropyrimidin-2(1H)-ones/thiones under Ultrasonic Irradiation", Biol. Pharm. Bull. 39, 267-271, (2016).
Lennon et al., "Metal Fluorides, Metal Chlorides and Halogenated Metal Oxides as Lewis Acidic Heterogeneous Catalysts. Providing Some Context for Nanostructured Metal Fluorides", Molecules, 22, (201.), 1, (2017).
Jones et al., "Cannabidiol", Acta Cryst,. B33, 3211-3214, (1977).
Keasling et al., "Yeast produce low-cost, high quality cannabinoids", Science Daily, 1-6, (2019).
World Health Organization, "Cannabidiol (CBD) Pre-Review Report: Expert Committee on Drug Dependence Thirty-Ninth Meeting", 1-27, (2017).
Bloemendal et al., "Synthetic pathways to tetrehydrocannabinol (THC): an overview", Royal Society of Chemistry, 1-13, (2020).

(Continued)

*Primary Examiner* — Sikarl A Witherspoon
(74) *Attorney, Agent, or Firm* — Nixon Peabody LLP; Ronald I. Eisenstein; Ravinderjit Braich

(57) ABSTRACT

Herein are described apparatus and processes for the preparation of cannabinoids, such as cannabidiol (CBD) and derivatives thereof. The apparatus and processes described can be used for the one-step, flow-mediated synthesis of cannabidiol and derivatives with improved overall yield, material throughput, and product purity relative to batch processes.

30 Claims, 9 Drawing Sheets

(56) References Cited

OTHER PUBLICATIONS

Giorgi et al., "Biomimetic Cannabinoid Synthesis Revisted: Batch and Flow All Catalytic Synthesis of ()-ortho-Tetrahydrocannabinols and Analogues from Natural Feedstocks", European Journal of Organic Cemistry, 1307-1311, (2018).
Lago-Fernandez et al., "New Methods for the Synthesis of Cannabidiol Derivatives", Methods Enzymol., 593, 237-257, (2017).
Petrzilka et al., "Synthese von Haschisch-Inhaltsstoffen 4", Mitteilung, Helv Chim Acta., 52, (4.), 1102-34, (1969).
Razdan et al., "A simple one-step synthesis of (−)-delta1-tetrahydrocannabinol (THC) from p-mentha-2,8-dien-1-ol and olivetol", J Am Chem Soc., 96, (18.), 5860-5865, (1974).
Baek et al., "Boron trifluoride etherate on alumina—a modified Lewis acid reagent ; An improved synthesis of cannabidiol", Tetrahedron Lett., 26, (8.), 1083, (1985).
Luo et al., "Complete biosynthesis of cannabinoids and their unnatural analogues in yeast", Nature, 567, (7746.), 123-126, (2019).
Shultz et al., "Enantioselective Total Synthesis of Cannabinoids—A Route for Analogue Development", Org Lett., 20, 381-384, (2018).
Gomez, "Hemp CBD Market to Reach $22 Billion by 2022: Outpacing the Rest of the Cannabis Market Combined 2018", www.brightfieldgroup.com/post/hemp-cbd-market-to-reach-22-billion-by-2022, (2019).
Gong et al., "Synthesis of CBD and Its Derivatives Bearing Various C4'-Side Chains with a Late-Stage Diversification Method", J. Org. Chem., 85, 4, 2704-2715, (2020).
Ben-Shabat et al., "New cannabidiol derivatives: synthesis, binding to cannabinoid receptor, and evaluation of their antiinflammatory activity", . J Med Chem., 49, (3.), 1113-1117, (2006).
Shinde et al., "Succinyl-β-cyclodextrin-driven synthesis of a nitrogen-fused five-ring heterocycle using GBB-based [4+1] cycloaddition via supramolecular host-guest interactions", Tetrahedron, 75, (6.), 778-783, (2019).
Liu et al., "Hydrophobic Solid Acids and Their Catalytic Applications in Green and Sustainable Chemistry", ACS Catalysis, 8, (1.), 372-391, (2018).
Crombie et al., "Terpenylations using (R)-(−)-α-phellandrene. Synthesis of the (3S,4R)-8,9-dihydro-o- and -p-cannabidiols, their iso-THC's, and the natural dihydrochalcone (3S,4R)-(+)-linderatin", Journal of the Chemical Society, Perkin Transactions, 1, (5.), 1251-1253, (1998).
Dauben et al., "Preparation of conjugated dienes from tosylhydrazones of .alpha.,.beta.-unsaturated ketones and alkyllithium reagents", Journal of the American Chemical Society, 90, (17.), 4762-4763, (1968).
Chakraborit et al., "Protic Acid Immobilized on Solid Support as an Extremely Efficient Recyclable Catalyst System for a Direct and Atom Economical Esterification of Carboxylic Acids With Alcohols" J. Org. Chem., 74, (16.), 5967-5974, (2009).
Da Silva et al., "Xanthenones: calixarenes-catalyzed syntheses, anticancer activity and QSAR studies", Org. Biomol. Chem., 13, (11.), 3280-3287, (2015).
Britton et al., "Multi-step Continuous Flow system", Chemical Society Rev., 46, 1250-1271, (2017).
International Search Report, PCT/US2020/28091 (Trustees of Boston Univ.) dated Jul. 20, 2020.

ONE-STEP FLOW-MEDIATED SYNTHESIS OF CANNABIDIOL (CBD) AND DERIVATIVES

RELATED APPLICATIONS

This application claims benefit under 35 U.S.C. § 119(e) of the U.S. Provisional Application No. 62/834,036 filed Apr. 15, 2019, the content of which is incorporated herein by reference in its entirety.

FIELD OF THE INVENTION

This invention relates to processes for the preparation of cannabidiol (CBD) and derivatives thereof. More particularly, the invention is directed to a process for the one-step, flow-mediated synthesis of cannabidiol (CBD) and derivatives with improvements relative to the corresponding batch processes.

BACKGROUND

The two major phytocannabinoids isolated from *Cannabis sativa* are (−)-trans-Δ9-tetrahydrocannabinol (THC) and (−)-cannabidiol (CBD). CBD can also be obtained from industrial hemp with contamination by low levels (0.03%) of residual THC. CBD is a promising and well-studied medicinal and therapeutic compound. Unlike THC which has relevant side effects and psychoactive activity, CBD is a non-psychoactive phytocannabinoid. CBD has been shown to have anti-anxiety, antidepressant, antipsychotic, anticonvulsant, anti-nausea, antioxidant, anti-inflammatory, anti-arthritic, and anti-neoplastic activity and is protective in animal models of epilepsy, anxiety, psychosis, and basal ganglia diseases [Ligresti A., De Petrocellis L., Di Marzo V., *From Phytocannabinoids to Cannabinoid Receptors and Endocannabinoids: Pleiotropic Physiological and Pathological Roles Through Complex Pharmacology*; Physiol Rev. 2016; 96(4):1593-659)]. CBD interacts with cannabinoid receptors in the immune system and non-psychoactive sites in the brain. Along these lines, Epidiolex® [Sekar K., Pack A., *Epidiolex as adjunct therapy for treatment of refractory epilepsy: a comprehensive review with a focus on adverse effects;* F1000Res. 2019; 8. PMCID: PMC6396837], an isolated pure form of CBD developed by GW Pharmaceuticals is currently in clinical trials for treatment-resistant seizure disorders such as Lennox-Gastaut and Dravet syndromes and was approved by the FDA in November 2018. More recently, the Drug Enforcement Administration (DEA) placed Epidiolex into Schedule V as a controlled substance relative to hemp-derived material containing residual THC which is listed under Schedule I. In addition to CBD, analogues such as the CBD homologue cannabidiphorol (CBDP) are also of current interest [Citti C., et al., *A novel phytocannabinoid isolated from Cannabis sativa L. with an in vivo cannabimimetic activity higher than Δ9-tetrahydrocannabinol: Δ9-Tetrahydrocannabiphoro;* Nature|Scientific Reports 2019 9:20335].

Regarding the chemical synthesis of CBD, a recent review summarizes major advances [Lago-Fernandez A., Redondo V., Hernandez-Folgado L., Figuerola-Asencio L., Jagerovic N. *New Methods for the Synthesis of Cannabidiol Derivatives;* Methods Enzymol. 2017; 593:237-57]. The stereospecific synthesis of (−)-CBD can be achieved by condensation of olivetol with (+)-p-mentha-2,8-dien-1-ol in presence of formamide acetal as a weak acid [Petrzilka T., Haefliger W., Sikemeier C., *Synthese von Haschisch-Inhaltsstoffen 4. Mitteilung;* Helv Chim Acta. 1969; 52(4):1102-34]. Also, use of boron trifluoride etherate instead of formamide acetal affords (−)-CBD in good yield [Razdan R. K., Dalzell H. C., Handrick G. R. *Hashish. A simple one-step synthesis of (−)-delta1-tetrahydrocannabinol (THC) from p-mentha-2,8-dien-1-ol and olivetol;* J Am Chem Soc. 1974; 96(18):5860-5]. One issue in the latter synthesis is the formation of the synthetic regioisomer, "abnormal CBD," as a byproduct. Modification of this last procedure with boron trifluoride etherate on alumina prevents the formation of this byproduct [Baek S.-H., Srebnik M., Mechoulam R., *Boron trifluoride etherate on alumina—a modified Lewis acid reagent;* An improved synthesis of cannabidiol. Tetrahedron Lett. 1985; 26(8):1083-6]. It has also been recognized that abnormal CBD (abn-CBD) or analogs are also of interest as therapeutics and provide benefits such as anti-inflammatory and anti-neurodegenerative effects [von Widdern J. C., Hohmann T., Dehghani F. *Abnormal Cannabidiol Affects Production of Pro-Inflammatory Mediators and Astrocyte Wound Closure in Primary Astrocytic-Microglial Cocultures;* Molecules 2020, 25(3), 496: Tomko A., et al., *Antitumor Activity of Abnormal Cannabidiol and Its Analog O-1602 in Taxol-Resistant Preclinical Models of Breast Cancer;* Front. Pharmacol., 27 Sep. 2019].

Recent reports from the Keasling lab at UC Berkeley have reported biosynthetic engineering of milligram amounts of the cannabinoids $\Delta^9$-tetrahydrocannabinolic acid (THCA), cannabidiolic acid (CBDA) (a precursor to CBD), cannabigerolic acid, cannabidiolic acid, $\Delta^9$-tetrahydrocannabivarinic acid, and cannabidivarinic acid in *Saccharomyces cerevisiae* (yeast) from the simple sugar galactose [Luo X., Reiter M. A., d'Espaux L., Wong J., Denby C. M., Lechner A., *Complete biosynthesis of cannabinoids and their unnatural analogues in yeast;* Nature. 2019; 567 (7746): 123-6.]. The investigators were also able to seed different fatty acids to engineered strains yielding cannabinoid analogues with modifications in the part of the molecule that is known to alter receptor binding affinity and potency.

U.S. Pat. 10,059,683 B2 (issued Aug. 28, 2018) describes a three step process for the preparation of a cannabidiol compound or derivative by an acid-catalyzed reaction of a dihalo-olivetol derivative with a suitably selected and substituted cyclic allylic alcohol such as mentha-2,8-dien-1-ol to produce a dihalo-cannabidiol compound or derivative which may then be converted by reduction to a cannabidiol or derivative. The reaction was conducted up to 7 g scale with purification of the final CBD material by silica gel column chromatography.

Koch et. al. in WO 2015032519 and WO2016135308A1 describe an overall three-step preparation of mixtures of cannabinoid derivatives useful for therapeutic treatment by the acid-catalyzed reaction of 6-alkyl-2,4-dihydroxybenzoic acid esters (e.g. olivetolic acid methyl or ethyl ester) with menthadienol followed by transesterification and decarboxylation.

Gu et. al. in WO 2004092101 A2 20041028, describe a regioselective process for the synthesis of Δ9-tetrahydrocannabinol A using a cyclodextrin-olivetol complex which is followed by reaction of the complex with a cyclic allylic alcohol terpene such as menthadienol to produce a cannabinoid.

Leahy et. al. in US 20190023680 A1 describes synthetic processes and intermediates for preparing cannabinoids and analogues using up to ten step reaction sequences [Shultz Z. P., Lawrence G. A., Jacobson J. M., Cruz E. J., Leahy J. W., *Enantioselective Total Synthesis of Cannabinoids-A Route for Analogue Development;* Org Lett. 2018; 20:381-4].

Gong el al. describe synthetic routes for CBD and derivatives bearing various C4'-side chains wherein the five-step synthesis provides a 52% yield of CBD on a 10 g scale [Gong. X. et al., *Synthesis of CBD and Its Derivatives Bearing Various C4'-Side Chains with a Late-Stage Diversification Method; J. Org. Chem.* 2020, 85, 2704-2715]. Such lengthy, multistep syntheses can be useful to produce novel CBD, CBD analogues or THC analogues on small (milligram and gram) scales for biological studies but are deemed impractical for bulk, multi-kilogram preparation of these cannabinoids.

In terms of the overall market demand for cannabidiol (CBD), the Chicago-based Brightfield Group, which performs consumer market research, estimates a projected CBD market of $22B in 2022 [Gomez B., *Hemp CBD Market to Reach $22 Billion by 2022: Outpacing the Rest of the Cannabis Market Combined* 2018, Available at: www.brightfieldgroup.com/post/hemp-cbd-market-to-reach-22-billion-by-2022, accessed Mar. 24, 2019]. This projected figure corresponds to a demand of 1.8 million kilograms of CBD for market areas include pharmaceuticals, nutraceuticals, skincare, pets, shampoo, hair coloring, soft drinks, and beer/cider infusions. Such demand requires a method for the chemical synthesis and production of CBD which is amenable to scale-up to mega-kilogram quantities.

Therefore, there is an ever growing need for an efficient method for the synthesis of CBD and CBD analogues and cannabinoids in general. The method also should be scalable to the kilogram or larger scale. Methods with minimal amounts of toxic or difficult to remove byproducts so that the product meets active pharmaceutical ingredient (API) quality standards are also desirable.

SUMMARY

In general, the inventions described herein relate to cannabinoids, and their preparation. The processes and systems include continuous processes wherein the starting reagents flow through a packed-bed reactor (PBR) containing a catalyst followed by elution of a product stream containing the desired cannabinoid. The systems and processes provide an efficient one-step preparation of cannabinoids such as CBD and derivatives.

In one aspect, a process for the preparation of a cannabidiol (CBD) or a derivative thereof is described. The process comprises providing a first compound that is a 1,3-diene or an allylic alcohol or an allylic ether and a second compound of Formula (IIA) or (IIB) into a packed-bed reactor (PBR) comprising a solid or heterogeneous catalyst; circulating the first and second compound through the PBR to react the first compound with the second compound; and collecting from the PBR a solution comprising the CBD or a derivative thereof. Optionally, the first compound has a structure selected from the group consisting of (IIIA), (IIIB), (IIIC), (IIID), and (IIIE). Optionally, the CBD or the derivative thereof has a structure selected from the group consisting of (IA), (IB), (IC), (ID), (IE), and (IF). Structures of (IA)-(IF), (IIA), (IIB) and IIId (IIIA)-(IIIE) are as follows:

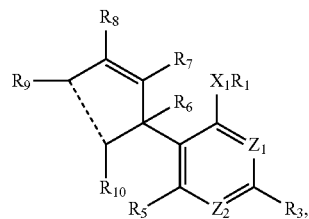

(IA)

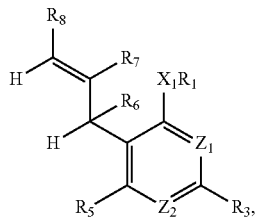

(IB)

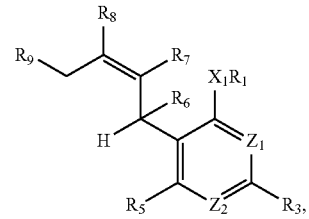

(IC)

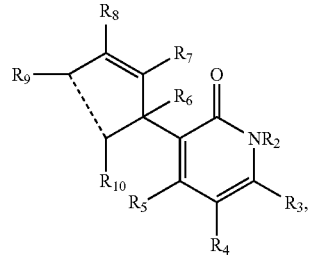

(ID)

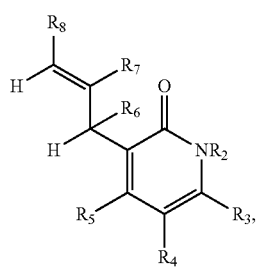

(IE)

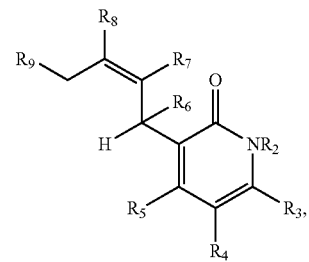

(IF)

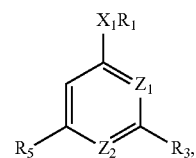

(IIA)

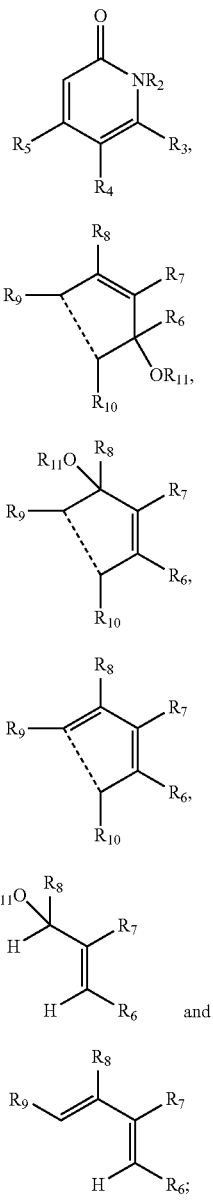

or a pharmaceutically acceptable salt or ester thereof.

Structures (IA)-(IF), (IIA)-(IIB) and (IIIA)-(IIIE), are further defined wherein: $Z_1$ is $CR_2$ or N; $Z_2$ is $CR_4$ or N; $R_1$, $R_2$, $R_3$, $R_4$, $R_5$, $R_6$, $R_7$, $R_8$, $R_9$, $R_{10}$, and $R_{11}$ are each independently selected from the group consisting of H, OH, —$CO_2H$, protected hydroxyl, alkyl, alkenyl, alkynyl, acyl, aryl, heteroaryl, cycloalkyl, heterocycle, —$X_2R^K$, or halides. The alkyl, alkenyl, alkynyl, or acyl group is optionally substituted with one or more substituents independently selected from the group consisting of halogen, —OH, alkyl, O-alkyl, —$NR^AR^B$, —S-alkyl, —SO-alkyl, —$SO_2$-alkyl, alkenyl, alkynyl, aryl, heteroaryl, cycloalkyl, or heterocycle; wherein the alkenyl, alkynyl, or acyl group optionally includes —O—, —S—, —$SO_2$—, —$N(R^G)$— substituting one or more carbons in the carbon chain, and wherein the aryl or heteroaryl, whether alone or as part of a substituent group, is optionally substituted with one or more substituents independently selected from the group consisting of halogen, OH, alkyl, O-alkyl, —COOH, —C(O)—$C_{1-4}$ alkyl, —C(O)O—$C_{1-4}$ alkyl, —$NR^CR^D$, —S-alkyl, —SO-alkyl and —$SO_2$-alkyl. $X_1$ is selected from —O—, —S—, —$SO_2$—, —$N(R^E)$— and $X_2$ is selected from —O—, —S—, —$SO_2$—, —$N(R^F)$. The dashed line ( ----- ) indicates a bond that is absent or a $C_{1-3}$ alkylene linker, which links the carbon bonded to $R_9$ and the carbon bonded to $R_{10}$. Furthermore, $R^A$, $R_B$, $R^C$, $R^D$, $R^E$, $R^F$, $R^K$ and $R^G$ are each independently selected from hydrogen and $C_{1-4}$ alkyl.

Optionally one or more of $R_2$, $R_3$, $R_4$ or $R_5$ is —$CO_2H$ and the process further comprising a decarboxylation step. Optionally, $R_2$ is —$CO_2H$ and the process further comprising a decarboxylation step. For example, the decarboxylation step comprises continuous flow thermolysis.

Optionally, at least one of $R_2$ and $R_4$ (or both) is not a halide. For example, $R_2$, and $R_4$, are each independently selected from the group consisting of H, OH, —$CO_2H$, protected hydroxyl, alkyl, alkenyl, alkynyl, acyl, aryl, heteroaryl, cycloalkyl, heterocycle, and —$X_2R^K$.

Optionally the process is a process further comprising diluting the solution comprising the CBD or derivative thereof. For example, wherein said diluting produces a two phase solution, having a first and second phase, wherein the first phase has a higher concentration of CBD or derivative thereof. Optionally, the process is a process further comprising separating the first phase from the second phase. For example, optionally, wherein said separating comprises a membrane separation step.

Optionally, the process for preparation of CBD or derivative thereof is a process further comprising separation of CBD or a derivative thereof from the solution comprising CBD or derivative thereof. Optionally, wherein separating comprise a membrane separation step. Optionally, the process is a process further comprising isolating CBD or derivative thereof using a method selected from crystallization, concentration, distillation, drying, spray drying, precipitation, chromatographic separation, extraction, filtering, or combinations thereof. In some embodiments, the separation can be assisted by esterification with a t-Boc-amino acid, such as tryptophan, alanine, glutamine, phenylalanine then followed post separation by basic hydrolysis to obtain purified CBD or derivative thereof, such as dihydro CBD, abnormal CBD, CBD, CBDP, CBG or other cannabinoid derivatives.

Optionally, the process for preparation of CBD or derivative thereof is a process wherein the solid acid or heterogeneous acid catalyst is selected from the group consisting of large- and medium-pore zeolites, aluminosilicates, Nafion-NR50, sulfated zirconia, silica gel, polyaniline sulfate, graphene oxide (GO), carboxylic acid functionalized GO (GO-$CO_2H$), polymer-supported boronic acids, heteropolyacids, tungstated zirconia, heterogeneous sulfonic acids, supported Lewis acid catalysts, β-cyclodextrin, and β-cyclodextrin-derivatives. Optionally, the large- and medium-pore zeolite catalyst is Zeolite HY or Zeolite Y0. Optionally, the aluminosilicate-packed bed is Montmorillonite K10 or KSF clay. Optionally, a heterogeneous sulfonic acid is selected from the group consisting of amorphous carbon-bearing supported sulfonic acids, sulfonic acid-functionalized mesoporous silica (SBA-Pr—$SO_3H$), boron sulfonic acid, sulfated tin oxide, and polystyrene-supported sulfonic acid resins. For example, optionally the polystyrene-supported sulfonic acid resin is a gel resin, such as optionally wherein the gel resin is Amberlyst-15. Optionally the polystyrene-supported sulfonic acid resin is a macroporous resin such as macroporous-TsOH (MP-TsOH). Optionally the Lewis acid catalyst is supported on a high-surface-area solid. For example, optionally the Lewis acid is selected from the group consisting of $AlCl_3$, $BF_3$, $SnCl_4$, and $TiCl_4$. Optionally the high-surface-area solid for supporting the Lewis acid is selected from the group consisting of graphite, $Al_2O_3$, MCM-41 $SiO_2$, zeolites, and acidic clays. Optionally the supported Lewis acid catalyst is chlorinated or fluorinated alumina ($Al_2O_3$) or $AlCl_3$ immobilized on mesoporous MCM-41 silica. Optionally, the β-cyclodextrin-derivative is β-cyclodextrin-butane sulfonic acid, β-cyclodextrin-propyl sulfonic acid, or β-cyclodextrin. Optionally, the supported catalyst can be comprised of a β-cyclodextrin-derivative supported on Dowex resin. Optionally, protic acids on solid supports can be used such as perchloric acid immobilized on silica gel ($HClO_4$—$SiO_2$) or fluoroboric acid immobilized on silica gel ($HBF_4$—$SiO_2$). Optionally, the supported catalyst can be comprised of a sulfonic acid-substituted calix[x] arene derivative supported on polystyrene, silica, controlled pore glass, or other solid support. Optionally the substituted calix[x]arene comprises a calix[8]arene sulfonic acid, calix[6]arene sulfonic acid, or calix[4]arene sulfonic acid.

Optionally, the compound of Formula (IA) is the compound of Formula (IV);

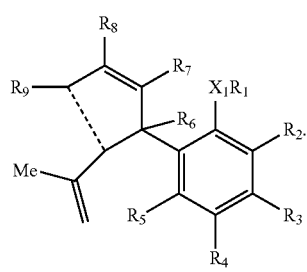

(IV)

Optionally $R_3$ is $X_2R^K$ or optionally $R_3$ is alkyl.

Optionally, the compound of Formula (IV) is (−)-cannabidiol (CBD) having the Formula (V);

1.

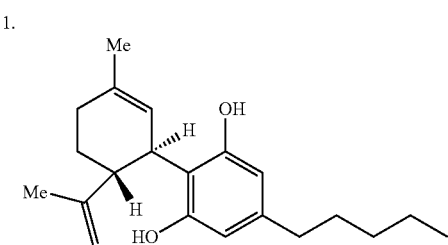

(V)

or optionally the compound of Formula (IV) is the abnormal-CBD, having the formula (V');

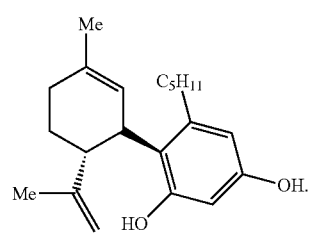

(V')

Optionally the compound of Formula (IA) is the compound of Formula (IV-$H_2$);

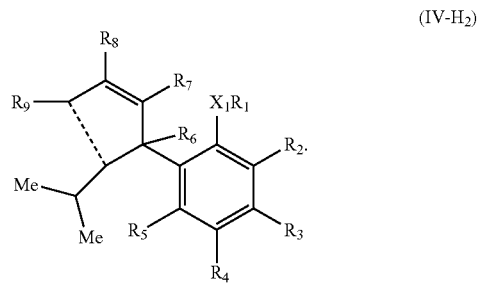

(IV-$H_2$)

Optionally $R_3$ is $X_2R^K$ or optionally $R_3$ is alkyl.

Optionally, the compound of formula (IV-$H_2$) is 8,9-dihydro CBD ($H_2$CBD) having formula (V-$H_2$);

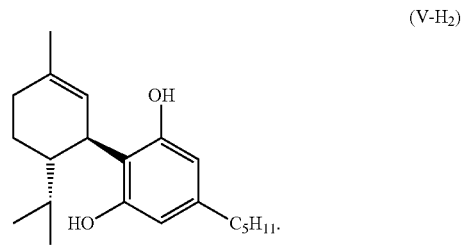

(V-$H_2$)

Optionally the compound of formula (IV-$H_2$) is abnormal dihydroCBD having formula (V'-$H_2$);

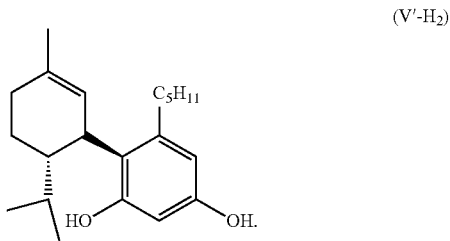

(V'-$H_2$)

Optionally the compound of Formula (IIA) is olivetol having the structure of Formula (VI), or olivetolic acid having the structure of Formula (VII);

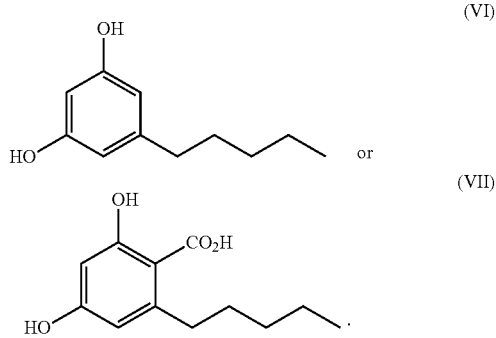

(VI)

or (VII)

Optionally, the compound of Formula (IIIB) is the compound having the structure (VIII);

(VIII)

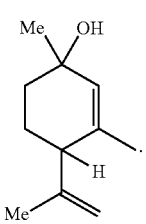

Optionally, the compound of Formula (VIII) is (+)-p-mentha-2,8-dien-1ol having the structure of Formula (IX);

(IX)

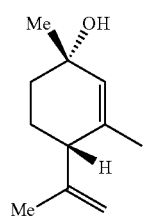

Optionally the compound of Formula (IIIC) is α-phellandrene having the structure of Formula (XII);

(XII)

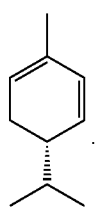

Optionally, compound of Formula (XII) is 2-methyl-5-isopropenyl-1,3-cyclohexadiene having the structure of Formula (XIII);

(XIII)

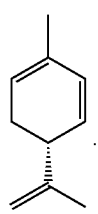

Some aspects described herein relate to automated, scalable, continuous flow reactor system for preparation of a CBD or derivative thereof; the system comprising: (a) one or more modular flow chemistry assembly lines; each assembly line comprising controlled input from one or more source pumps for reagents; at least one packed bed reactor (PBR); optionally, at least one heated reactor incorporating one or more membrane separators for waste $CO_2$; optionally, at least one back pressure regulator; optionally, at least one auxiliary pump; optionally, at least one membrane separator for waste water; and one or more collection tanks for compound CBD or derivative thereof.

In some embodiments, the system further comprises means for separating the CBD or derivative thereof prior to the one or more collection tanks. For example, following a packed bed reactor on the chemistry assembly line there are inserted modules comprising one or more silica normal phase chromatography columns for separating the CBD or cannabinoid derivatives. Such columns can be industrially scaled, for example, Novasep's Applexion SC. In some embodiments, the separation can be assisted by esterification with a t-Boc-amino acid such as tryptophan, alanine, glutamine, or phenylalanine followed post separation by basic hydrolysis to obtain purified compounds such as dihydro CBD, abnormal CBD, CBD, CBDP, CBG, or other cannabinoid derivatives.

Some other aspects described herein relate to a CBD compound or derivative made by the processes or systems described herein. Optionally the compound has the structure (IA). Optionally the compound has the structure (IB). Optionally the compound has the structure (IC). Optionally the compound has the structure (ID). Optionally the compound has the structure (IE). Optionally the compound has the structure (IF).

The processes and systems described herein provide many improvements over, for example, batch and laboratory prep scale processes. The process provides CBD or derivative thereof with minimal amounts of any toxic or difficult to remove byproducts. The process is also readily scalable; that is, CBD or derivative thereof can be made in a large scale production, such as multigram, kilogram, or greater amounts. Therefore, the processes enable one-step, flow-mediated synthesis of cannabinoids in good overall yield and high product purity that meets active pharmaceutical ingredient (API) quality standards without necessarily requiring additional purification steps.

DETAILED DESCRIPTION

Figure 1:
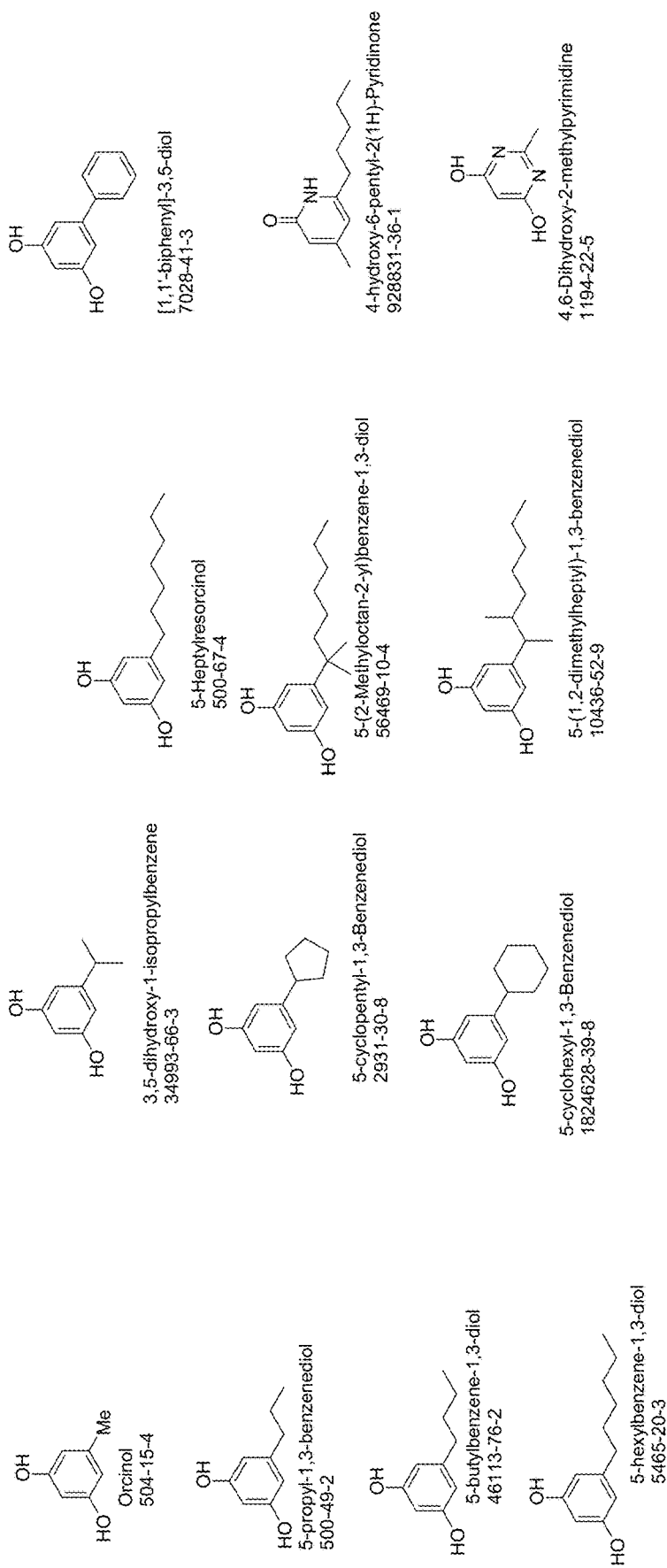
FIG. 1 Resorcinol-type reaction partners according to some embodiments and their CAS numbers.
Figure 1:
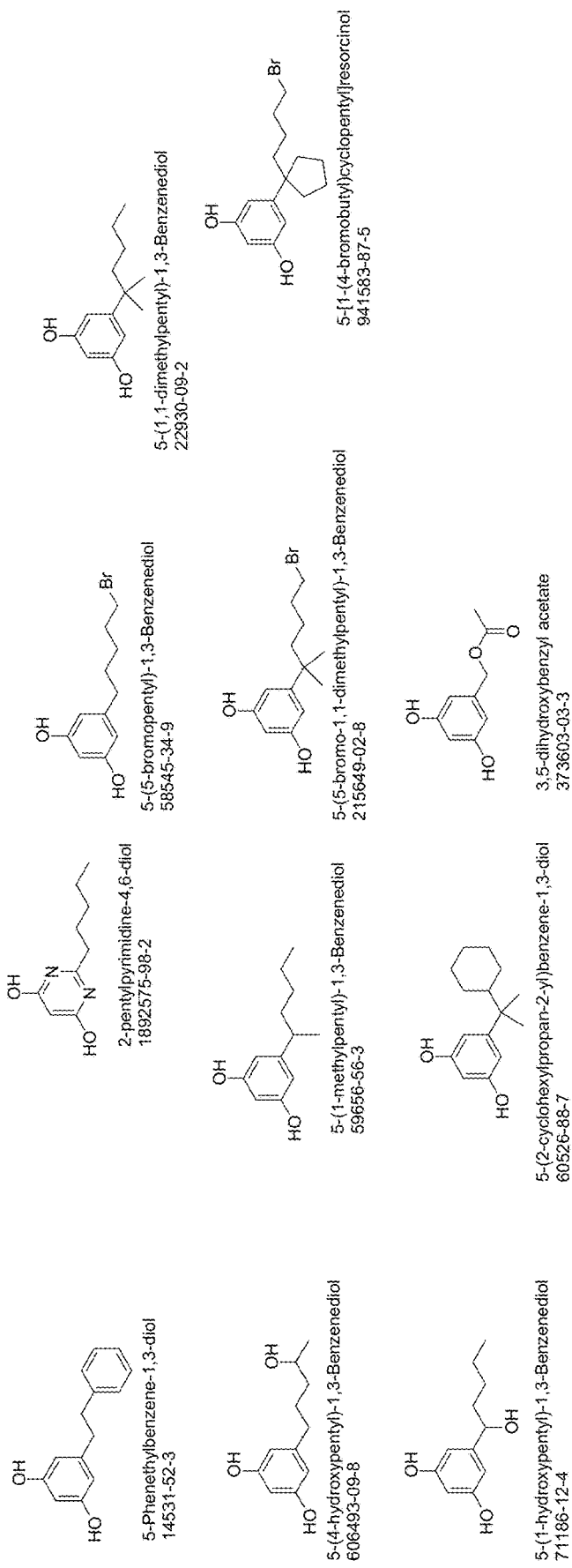

The present disclosure relates to a method and systems for the modular and scalable synthesis of cannabinoids such as CBD and derivatives using a continuous flow system. Without limitations, virtues of the one-step, flow-mediated synthesis of cannabidiol and derivatives are the improved overall yield, material throughput, and product purity relative to other batch-mediated protocols.

In some embodiments, an aromatic compound having Formula (IIA) is reacted with an oxygenated species having formula (IIIA) or (IIIB) in a single step reaction by flowing through a packed bed reactor (PBR) containing a solid or heterogeneous catalyst. The process provides a single step synthesis of compounds having Formula (IA) and nominally the alcohol $R_{11}OH$ as a byproduct as shown in Scheme 1.

Scheme 1

Reaction A

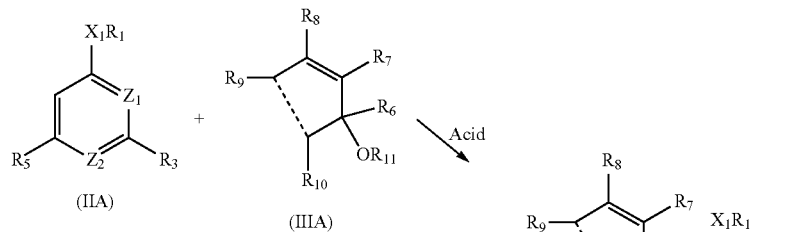

Reaction B

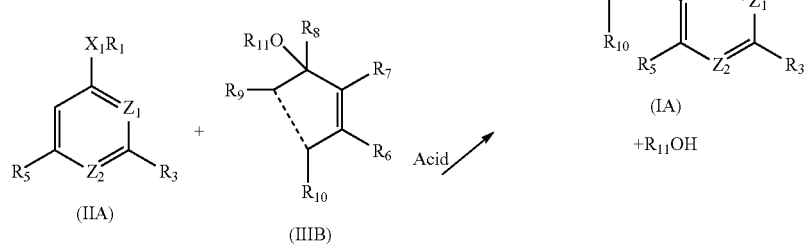

In Reaction A, an aryl carbon from (IIA) forms a bond with the α, or same carbon, that the $OR_{11}$ "leaving group" of (IIIA) is attached, thereby forming (IA). In Reaction B the aryl carbon from (IIA) forms a bond with a carbon γ to the $OR_{11}$ leaving group of (IIIB), also forming (IA). Without being bound by any specific mechanism, it is proposed that the selection of groups, such as the leaving group and other groups, can alter the mechanism due to steric and electronic effects. In some embodiments Reaction A is operational or dominant and compound (IIIA) is used. In some other embodiments Reaction B is operational and dominant and compound (IIIB) is used. As used here "dominant" relates to the rates, where the dominant reaction is at least 10 times higher (e.g. at least 100 times, at least 1,000 times) than a non-dominant reaction rate. Selection of either (IIIA) and (IIIB) is made so that the dominant path leads to a higher amount of product (I) than the alternative isomer from the non-dominant path.

In some embodiments an aromatic compound having Formula (IIB) is reacted with the oxygenated species having formula (IIIA) or (IIIB) using the PBR as described above. The reaction scheme is similar as in Scheme 1 as is depicted as Scheme 2. The process provides a single step synthesis of compounds having Formula (ID) and nominally the alcohol $R_{11}OH$ as a byproduct as shown.

Scheme 2

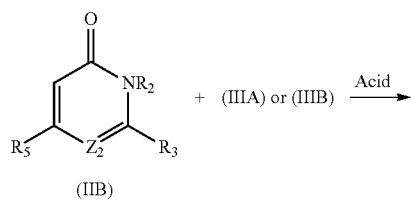

-continued

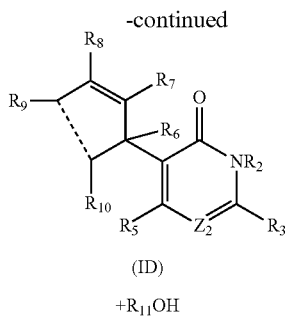

$+R_{11}OH$

In some other embodiments, as shown in Scheme 3 dienes (IIIC) are reacted (Reaction C) with an aromatic compound (IIA) to provide cannabinoid (IA), or the diene (IIIC) are reacted (Reaction D) with an aromatic compound (IIB) to provide cannabinoid (ID).

Scheme 3

Reaction C

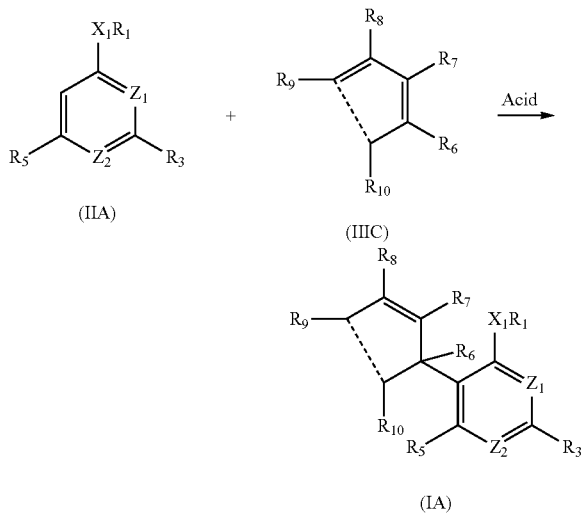

Reaction D

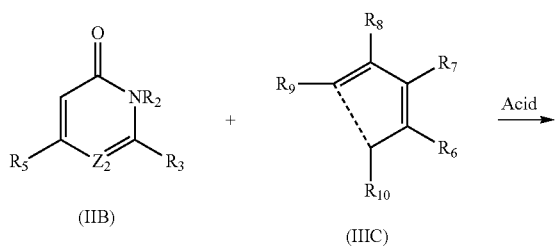

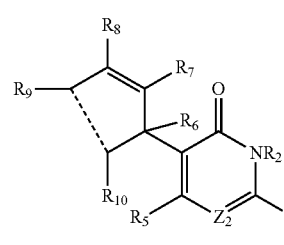

In some embodiments allylic alcohols, allylic ethers, and esters such as compound (IIID) are reacted with the aromatic compounds (IIA) or (IIB) as shown in Scheme 4 (Reaction E and Reaction F respectively). This provides the compounds (IB) by Reaction E and compounds (IE) by Reaction F.

Scheme 4

Reaction E

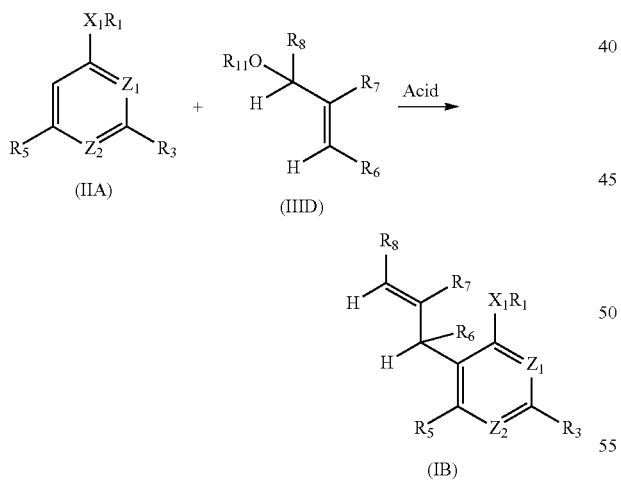

Reaction F

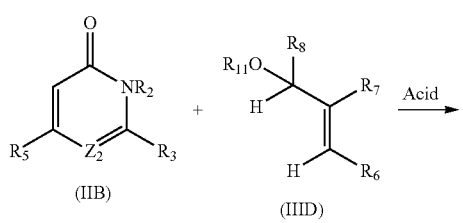

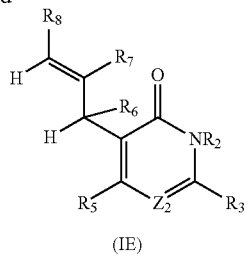

In some other embodiments, diene reagents such as (IIIE) are reacted with (IIA) or (IIB) as shown in Scheme 5 (Reaction G and Reaction H respectively). This provides the compounds (IC) by Reaction G and compounds (IF) by Reaction H.

Scheme 5

Reaction G

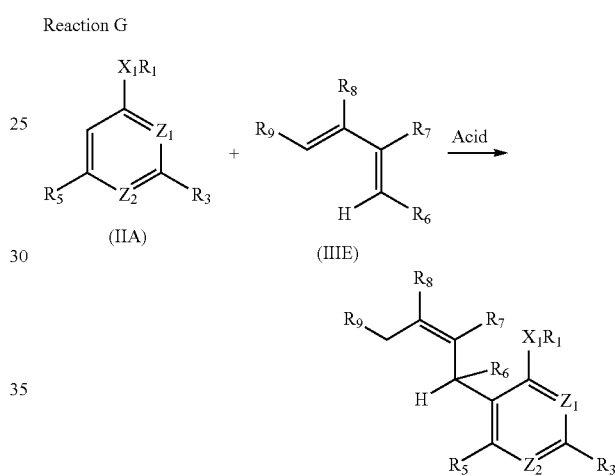

Reaction H

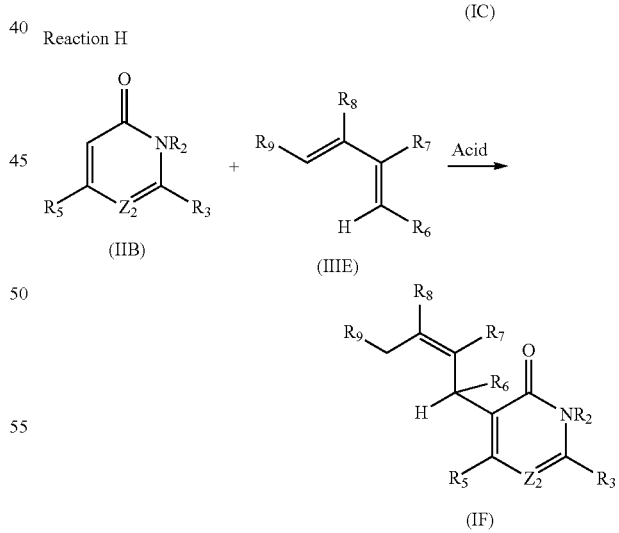

For the structures described herein, $Z_1$ can be N or $CR_2$ and $Z_1$ can be N or $CR_4$. $R_1$, $R_3$, $R_5$, $R_6$, $R_7$, $R_8$, $R_9$, $R_{10}$ and $R_{11}$ are each independently selected from the group consisting of H, OH, —$CO_2H$, protected hydroxyl, alkyl, alkenyl, alkynyl, acyl, aryl, heteroaryl, cycloalkyl, heterocycle, —$X_2R^K$, or halides. $R_2$, and $R_4$, are each independently selected from the same groups as $R_1$, $R_3$, $R_5$, $R_6$, $R_7$, $R_8$, $R_9$, $R_{10}$ and $R_{11}$ except that $R_2$, and $R_4$ are not selected from halides. In some optional embodiments $R_1$, $R_3$, $R_5$, $R_6$, $R_7$, $R_8$, $R_9$, $R_{10}$ and $R_{11}$ also do not include any halides. The alkyl, alkenyl, alkynyl, or acyl is optionally substituted with one or more substituents independently selected from the group consisting of halogen, —OH, alkyl, O-alkyl, —NR$^A$R$^B$, —S-alkyl, —SO-alkyl, —SO$_2$-alkyl, alkenyl, alkynyl, aryl, heteroaryl, cycloalkyl or heterocycle, and the alkenyl, alkynyl, or acyl group optionally includes —O—, —S—, —SO$_2$—, —N(R$^G$)-substituting one or more carbons in the carbon chain, and wherein the aryl or heteroaryl, whether alone or as part of a substituent group, is optionally substituted with one or more substituents independently selected from the group consisting of halogen, OH, alkyl, O-alkyl, —COOH, —C(O)—C$_{1-4}$ alkyl, —C(O)O—C$_{1-4}$ alkyl, —NR$^C$R$^D$, —S-alkyl, —SO-alkyl and —SO$_2$-alkyl. $X_1$ is selected from —O—, —S—, —SO$_2$—, —N(R$^E$)— and $X_2$ is selected from —O—, —S—, —SO$_2$—, —N(R$^F$). In the structures described herein the dashed line ----- indicates a bond that is absent or alternatively a $C_{1-3}$ alkylene linker, which links the carbon bonded to $R_9$ and the carbon bonded to $R_{10}$. For example, ----- is optionally —(CH$_2$)$_n$—, wherein n is 1, 2 or 3. In some embodiments, ----- is methylene, i.e., —CH$_2$—. Furthermore, R$^A$, R$_B$, R$^C$, R$^D$, R$^E$, R$^F$, R$^G$ and R$^K$ are each independently selected from hydrogen and C$_{1-4}$ alkyl.

As used herein, the term "alkyl", whether alone or as part of a substituent group, refers to a saturated $C_1$-$C_n$ carbon chain, wherein the carbon chain can be straight or branched; wherein the number of carbons in the chain can be 1, 2, 3, 4, 5, 6, 7, 8, 9 or 10. Suitable examples include, but are not limited to methyl, ethyl, propyl, isopropyl, butyl, isobutyl, sec-butyl, tert-butyl, n-pentyl and n-hexyl.

As used herein, the term "alkenyl", whether alone or as part of a substituent group, refers to a $C_2$-$C_n$ carbon chain, wherein the carbon chain can be straight or branched, wherein the carbon chain contains at least one carbon-carbon double bond, and wherein the number of carbons in that chain can be 2, 3, 4, 5, 6, 7, 8, 9, or 10.

As used herein, the term "alkynyl", whether alone or as part of a substituent group, refers to a $C_2$-$C_n$ wherein the carbon chain can be straight or branched, wherein the carbon chain contains at least one carbon-carbon triple bond, and wherein the number of carbons in the chain can be 2, 3, 4, 5, 6, 7, 8, 9, or 10.

As used herein, the term "aryl", whether alone or as part of a substituent group, refers to an unsubstituted carbocylic aromatic ring comprising between 6 to 14 carbon atoms. Suitable examples include, but are not limited to, phenyl, and naphthyl.

As used herein, the term "protected hydroxyl" refers to a hydroxyl group substituted with a suitably selected oxygen protecting group. More particularly, a "protected hydroxyl" refers to a substituent group of the Formula OPG wherein PG is a suitably selected oxygen protecting group. During any of the processes for preparation of the compounds of the present disclosure it can be necessary and/or desirable to protect sensitive or reactive groups on any of the molecules concerned. This can be achieved by means of conventional protecting groups, such as those described in "Protective Groups in Organic Chemistry", ed. J. F. W. McOmie, Plenum Press, 1973; and T. W. Greene & P. G. M. Wuts, Protective Groups in Organic Synthesis, John Wiley & Sons, 1991. The protecting groups can be removed at a convenient subsequent stage using methods known from the art.

As used herein, the term "oxygen protecting group" refers to a group which can be attached to an oxygen atom to protect said oxygen atom from participating in a reaction and which can be readily removed following the reaction. Suitable oxygen protecting groups include, but are not limited to, acetyl, benzoyl, t-butyl-dimethylsilyl, trimethylsilyl (TMS), MOM, and THP. Other suitable oxygen protecting groups can be found in texts such as "Protective Groups in Organic Synthesis," T. W. Greene & P. G. M. Wuts, John Wiley & Sons, 1991.

As used herein, the term "nitrogen protecting group" refers to a group which can be attached to a nitrogen atom to protect the said nitrogen atom from participating in a reaction and which can be readily removed following the reaction. Suitable nitrogen protecting groups include, but are not limited to, carbamate groups of the Formula —C(O) O—R wherein R can be methyl, ethyl, tert-butyl, benzyl, phenylethyl, CH$_2$=CH—CH$_2$, and the like; amides groups of the Formula C(O)—R' wherein R' can be methyl, phenyl, trifluoromethyl, and the like; N-sulfonyl derivatives groups of the Formula SO$_2$—R" wherein R" can be tolyl, phenyl, trifluoromethyl, 2,2,5,7,8-pentamethylchroman-6-yl-, 2,3,6-trimethyl-4-methoxybenzene, and the like. Other suitable nitrogen protecting groups can be found in texts such as T. W. Greene & P. G. M. Wuts, "Protective Groups in Organic Synthesis", John Wiley & Sons, 1991.

As used herein, the term "acyl" refers to a group of the Formula CO—C$_n$ wherein C$_n$ represent a straight or branched alkyl chain wherein n can be 1, 2, 3, 4, 5, 6, 7, 8, 9, or 10.

As used herein, the term "heteroaryl" refers to any five or six membered monocyclic aromatic ring structure containing at least one heteroatom selected from the group consisting of O, N and S, and optionally containing one to three additional heteroatoms independently selected from the group consisting of O, N and S; or a nine- or ten-membered bicyclic aromatic ring structure containing at least one heteroatom selected from the group consisting of O, N and S, and optionally containing one to four additional heteroatoms independently selected from the group consisting of O, N, and S. The heteroaryl group can be attached at any heteroatom or carbon atom of the ring such that the result is a stable structure. Examples of suitable heteroaryl groups include, but are not limited to, pyrrolyl, furyl, thienyl, oxazolyl, imidazolyl, pyrazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl and pteridinyl.

As used herein, the term "heterocycle" refers to any four to six membered monocyclic ring structure containing at least one heteroatom selected from the group consisting of O, N and S, and optionally containing one to three additional heteroatoms independently selected from the group consisting of O, N and S; or an eight- to ten-membered bicyclic ring structure containing at least one heteroatom selected from the group consisting of O, N and S, and optionally containing one to four additional heteroatoms independently selected from the group consisting of O, N, and S. The heterocycle group can be attached at any heteroatom or carbon atom of the ring such that the result is a stable structure. Examples of suitable heterocycle groups include, but are not limited to, azetidine, azete, oxetane, oxete, thietane, thiete, diazetidine, diazete, dioxetane, dioxete, dithietane, dithiete, pyrrolidine, pyrrole, tetrahydrofuran, furan, thiolane, thiophene, piperidine, oxane, thiane, pyridine, pyran, and thiopyran.

The groups of the present disclosure can be unsubstituted or substituted, as herein defined. In addition, the substituted groups can be substituted with one or more groups such as a $C_1$-$C_6$ alkyl, $C_{1-4}$ alkyl, —O—$C_{1-4}$ alkyl, hydroxyl, amino, ($C_{1-4}$ alkyl)amino, di($C_{1-4}$ alkyl)amino, —S—($C_{1-4}$ alkyl), —SO—($C_{1-4}$ alkyl), —$SO_2$—($C_{1-4}$alkyl), halogen, aryl, heteroaryl, and the like.

With reference to substituents, the term "independently" means that when more than one of such substituents is possible, such substituents can be the same or different from each other.

The compounds of the present disclosure can contain at least one hydroxyl group. At least one hydroxyl group can form an ester with inorganic or organic acid, in particular, pharmaceutically acceptable acids. The derived ester(s) can also form chiral carbons. The present disclosure is directed toward all stereochemical forms of the compounds, including those formed by the formation of one or more ester groups.

In some embodiments, the compound of Formula (IA) is the compound having Formula (IV):

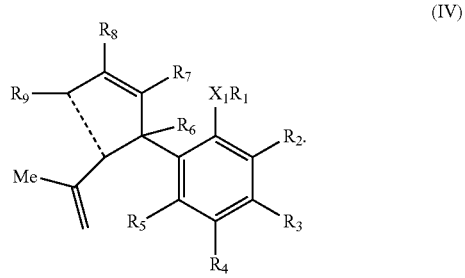

(IV)

Some embodiments include the "normal" structure wherein for the structure (IV): $X_1R_1$ and $R_5$ are hydroxyl; $R_6$, $R_7$, $R_9$ are hydrogen; $R_2$, $R_4$, $R_3$ and $R_8$ are independently selected from hydrogen, alkyl, alkenyl, alkynyl, acyl; and ----- is —$(CH_2)_n$ linker, where n is 1, 2 or 3. In some embodiments, n is 1, i.e., ----- is methylene (—$CH_2$—). As used herein, "normal" refers to structures where $X_1R_1$ and $R_5$ are hydroxyl and $R_3$ is not a hydroxyl, for example CBD has the normal structure.

In some embodiments having the normal structure (IV): $X_1R_1$ and $R_5$ are hydroxyl; $R_2$, $R_4$, $R_6$, $R_7$, $R_9$ are hydrogen; $R_3$ and $R_8$ are independently selected from an alkyl, alkenyl, alkynyl, acyl; and ----- is —$(CH_2)_n$ linker, where n is 1, 2 or 3. In some embodiments, n is 1, i.e., ----- is methylene (—$CH_2$—).

In some other embodiments of the normal structure (IV): $X_1R_1$ and $R_5$ are hydroxyl; $R_6$, $R_7$, $R_9$ are hydrogen; $R_2$, $R_4$, $R_3$ is independently selected from a hydrogen, alkyl or acyl; $R_8$ is an alkyl or an alkenyl; and ----- is —$(CH_2)$— linker.

In some other embodiments of the normal structure (IV): $X_1R_1$ and $R_5$ are hydroxyl; $R_2$, $R_4$, $R_6$, $R_7$, $R_9$ are hydrogen; $R_3$ is an alkyl or acyl, and $R_8$ is an alkyl or an alkenyl; and ----- is —$(CH_2)$— linker.

In some other embodiments of the normal structure (IV): $X_1R_1$ and $R_5$ are hydroxyl; $R_2$, $R_4$, $R_6$, and $R_7$ are hydrogen; $R_3$ is an alkyl or acyl; and $R_8$ is an alkyl (e.g., methyl); $R_9$ is an alkyl or an alkenyl; and ----- is —$(CH_2)$— linker.

In some embodiments of the normal structure (IV): $X_1R_1$ and $R_5$ are hydroxyl; $R_6$, and $R_7$ are hydrogen; $R_2$, $R_4$, $R_3$ are independently selected from hydrogen, alkyl or acyl; $R_8$ is a methyl; $R_9$ is an alkyl or an alkenyl; and ----- is missing, i.e., there is no linker connecting the carbons to which $R_9$ and $R_{10}$ are connected. In some other embodiments having structure (IV): $X_1R_1$ and $R_5$ are hydroxyl; $R_2$, $R_4$, $R_6$, and $R_7$ are hydrogen; $R_3$ is an alkyl or acyl; and $R_8$ is a methyl; $R_9$ is an alkyl or an alkenyl; and ----- is missing, i.e., there is no linker connecting the carbons to which $R_9$ and $R_{10}$ are connected.

Some embodiments include the abnormal structure wherein for the structure (IV): $X_1R_1$ and $R_3$ are hydroxyl; $R_6$, $R_7$, $R_9$ are hydrogen; $R_2$, $R_4$, $R_5$ and $R_8$ are independently selected from hydrogen, alkyl, alkenyl, alkynyl, acyl; and ----- is —$(CH_2)_n$ linker, where n is 1, 2 or 3. In some embodiments, n is 1, i.e., ----- is methylene (—$CH_2$—). As used herein, "abnormal" refers to structures where $X_1R_1$ and $R_3$ are hydroxyl and $R_5$ is not a hydroxyl, for example abnormal CBD has the abnormal structure.

In some embodiments having the abnormal structure (IV): $X_1R_1$ and $R_3$ are hydroxyl; $R_2$, $R_4$, $R_6$, $R_7$, $R_9$ are hydrogen; $R_5$ and $R_8$ are independently selected from an alkyl, alkenyl, alkynyl, acyl; and ----- is —$(CH_2)_n$ linker, where n is 1, 2 or 3. In some embodiments, n is 1, i.e., ----- is methylene (—$CH_2$—).

In some other embodiments of the abnormal CBD structure (IV): $X_1R_1$ and $R_3$ are hydroxyl; $R_6$, $R_7$, $R_9$ are hydrogen; $R_2$, $R_4$, $R_5$ is independently selected from hydrogen, alkyl or acyl; $R_8$ is an alkyl or an alkenyl; and ----- is —$(CH_2)$— linker.

In some other embodiments of the abnormal CBD structure (IV): $X_1R_1$ and $R_3$ are hydroxyl; $R_2$, $R_4$, $R_6$, $R_7$, $R_9$ are hydrogen; $R_5$ is an alkyl or acyl, and $R_8$ is an alkyl or an alkenyl; and ----- is —$(CH_2)$— linker.

In some other embodiments of the abnormal CBD structure (IV): $X_1R_1$ and $R_3$ are hydroxyl; $R_2$, $R_4$, $R_6$, and $R_7$ are hydrogen; $R_5$ is an alkyl or acyl; and $R_8$ is an alkyl (e.g., methyl); $R_9$ is an alkyl or an alkenyl; and ----- is —$(CH_2)$— linker.

In some embodiments of the abnormal CBD structure (IV): $X_1R_1$ and $R_3$ are hydroxyl; $R_6$, and $R_7$ are hydrogen; $R_2$, $R_4$, $R_5$ are independently selected from hydrogen, alkyl or acyl; $R_8$ is a methyl; $R_9$ is an alkyl or an alkenyl; and ----- is missing, i.e., there is no linker connecting the carbons to which $R_9$ and $R_{10}$ are connected. In some other embodiments having structure (IV): $X_1R_1$ and $R_3$ are hydroxyl; $R_2$, $R_4$, $R_6$, and $R_7$ are hydrogen; $R_5$ is an alkyl or acyl; and $R_8$ is a methyl; $R_9$ is an alkyl or an alkenyl; and ----- is missing, i.e., there is no linker connecting the carbons to which $R_9$ and $R_{10}$ are connected.

In some embodiments the compound of Formula (IA) is a compound having Formula (X):

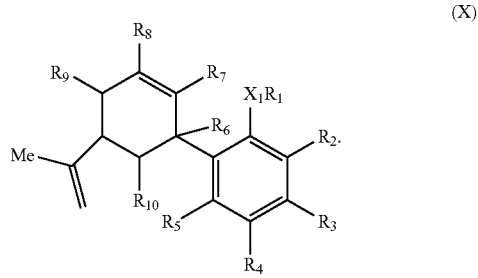

(X)

In some embodiments having structure having the normal structure for (X): $X_1R_1$ and $R_5$ are hydroxyl; $R_6$, $R_8$, $R_9$ are hydrogen; $R_2$, $R_4$, $R_3$ and $R_7$ are independently selected from hydrogen, alkyl, alkenyl, alkynyl, acyl. In some embodiments having structure (X): $X_1R_1$ and $R_5$ are hydroxyl; $R_2$, R$_4$, R$_6$, R$_8$, R$_9$ are hydrogen; and R$_3$ and R$_7$ are independently selected from an alkyl, alkenyl, alkynyl, and acyl. In some other embodiments having structure (X): X$_1$R$_1$ and R$_5$ are hydroxyl; R$_2$, R$_4$, R$_6$, R$_8$, and R$_9$ are hydrogen; R$_3$ is an alkyl or acyl, and R$_8$ is an alkyl (e.g. methyl).

In some embodiments having structure having the abnormal structure for (X): X$_1$R$_1$ and R$_3$ are hydroxyl; R$_6$, R$_8$, R$_9$ are hydrogen; R$_2$, R$_4$, R$_5$ and R$_7$ are independently selected from hydrogen, alkyl, alkenyl, alkynyl, acyl. In some embodiments having structure (X): X$_1$R$_1$ and R$_3$ are hydroxyl; R$_2$, R$_4$, R$_6$, R$_8$, R$_9$ are hydrogen; and R$_5$ and R$_7$ are independently selected from an alkyl, alkenyl, alkynyl, and acyl. In some other embodiments having structure (X): X$_1$R$_1$ and R$_3$ are hydroxyl; R$_2$, R$_4$, R$_6$, R$_8$, and R$_9$ are hydrogen; R$_5$ is an alkyl or acyl, and R$_8$ is an alkyl (e.g. methyl).

In some embodiments the compound of Formula (IA) is a compound having Formula (XI):

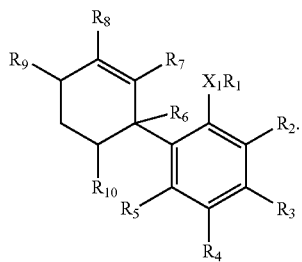

(XI)

In some embodiments having the normal structure (XI): X$_1$R$_1$ and R$_5$ are hydroxyl; R$_6$, R$_7$, R$_8$, R$_9$ are hydrogen; R$_2$, R$_4$, and R$_3$ are independently selected from hydrogen, an alkyl, alkenyl, alkynyl, acyl. In some embodiments having structure (XI): X$_1$R$_1$ and R$_5$ are hydroxyl; R$_2$, R$_4$, R$_6$, R$_7$, R$_8$, R$_9$ are hydrogen; and R$_3$ is selected from an alkyl, alkenyl, alkynyl, and acyl. In some embodiments having the normal structure for (XI), R$_{10}$ is an isopropene group, and in other embodiments R$_{10}$ is an isopropane group (hydrogenated normal structure).

In some embodiments having the abnormal structure (XI): X$_1$R$_1$ and R$_3$ are hydroxyl; R$_6$, R$_7$, R$_8$, R$_9$ are hydrogen; R$_2$, R$_4$, and R$_5$ are independently selected from hydrogen, an alkyl, alkenyl, alkynyl, acyl. In some embodiments having structure (XI): X$_1$R$_1$ and R$_3$ are hydroxyl; R$_2$, R$_4$, R$_6$, R$_7$, R$_8$, R$_9$ are hydrogen; and R$_5$ is selected from an alkyl, alkenyl, alkynyl, and acyl. In some embodiments having the abnormal structure for (XI), R$_{10}$ is an isopropene group, and in other embodiments R$_{10}$ is an isopropane group (hydrogenated abnormal structure).

Examples of compound (IIA) or (IIB) include but are not limited to 5-substituted resorcinols such as 5-propyl resorcinol (divarin) and 5-(1,1-dimethylheptyl)resorcinol and mono-ethers of phloroglucinol including 5-methoxyresorcinol. In some embodiments compound (IIA) is olivetol (VI) or olivetolic acid (VII). In some embodiments, the compounds (IIA) and (IIB) are resorcinol-type compounds shown with their CAS numbers in FIG. 1 and include but are not limited to orcinol, 3,5-dihydroxy-1-isopropylbenzene, 5-propyl-1,3-benzenediol, 5-cyclopentyl-1,3-benzenediol, 5-butylbenzene-1,3-diol, 5-hexylbenzene-1,3-diol, 5-cyclohexyl-1,3-benzenediol, 5-heptylresorcinol, 1,1'-biphenyl]-3,5-diol, 5-(2-methyloctan-2-yl)benzene-1,3-diol, 4-hydroxy-6-pentyl-2(1H)-pyridinone, 5-(1,2-dimethylheptyl)-1,3-benzenediol, 4,6-dihydroxy-2-methylpyrimidine, 5-phenethylbenzene-1,3-diol, 2-pentylpyrimidine-4,6-diol, 5-(4-hydroxypentyl)-1,3-Benzenediol, 5-(1-methylpentyl)-1,3-benzenediol, 5-(1-hydroxypentyl)-1,3-benzenediol, 5-(2-cyclohexylpropan-2-yl)benzene-1,3-diol, 5-(5-bromopentyl)-1,3-benzenediol, 5-(1,1-dimethylpentyl)-1,3-benzenediol, 5-(5-bromo-1,1-dimethylpentyl)-1,3-Benzenediol, 5-[1-(4-bromobutyl)cyclopentyl]resorcinol, and 3,5-dihydroxybenzyl acetate.

Figure 2:
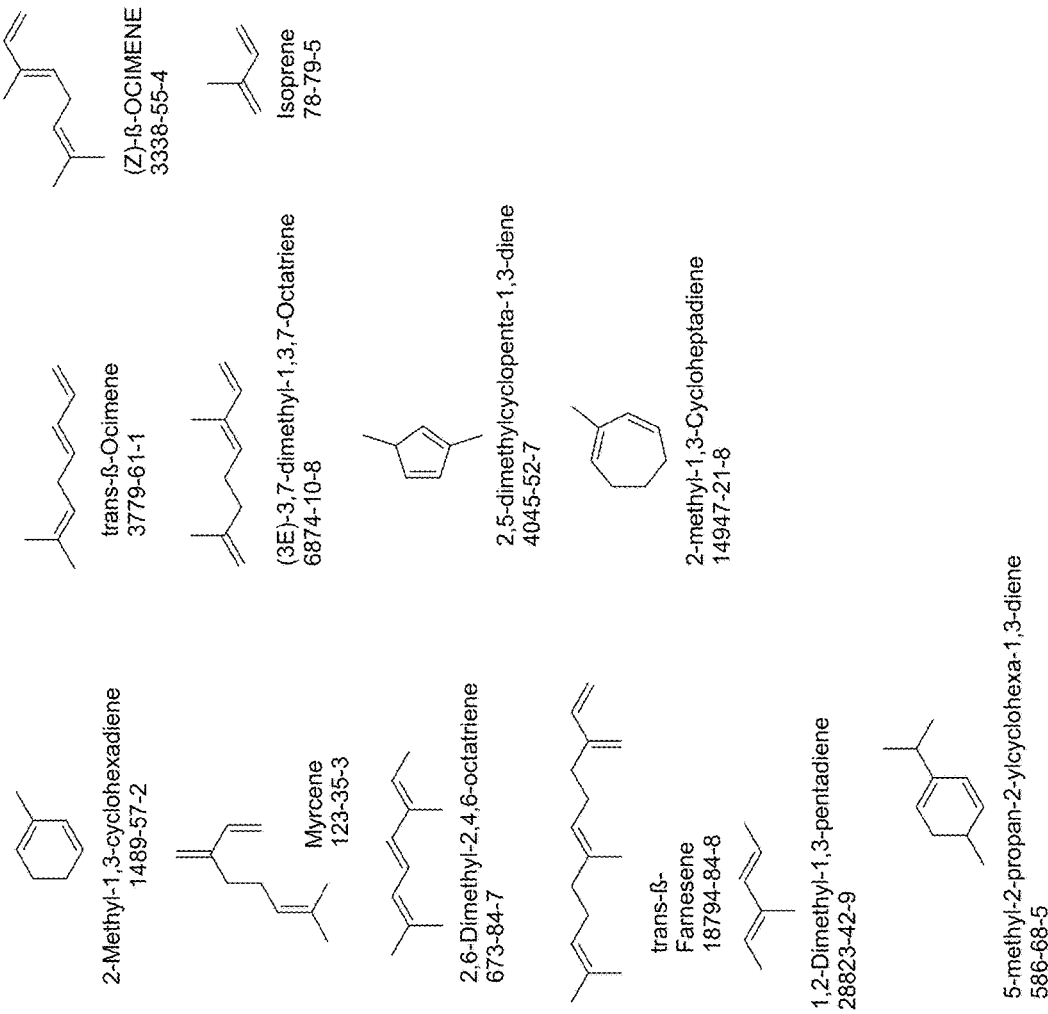
FIG. 2 Diene reaction partners according to some embodiments and their CAS numbers.

Examples of diene reactions partners (IIIC) and (IIIE) according to some embodiments include but are not limited to 2-methyl-1,3-cyclohexadiene, trans-β-ocimene, (Z)-β-ociment, myrcene, (3E)-3,7-dimethyl-1,3,7-octatriene, isoprene, 2,6-dimethyl-2,4,6-octatriene, 2,5-dimethylcyclopenta-1,3-diene, trans-β-farnesene, 2-methyl-1,3-cycloheptadiene, 1,2-dimethyl-1,3-pentadiene, and 5-methyl-2-propan-2-ylcyclohexa-1,3-diene. The structures and CAS numbers of these compounds are shown in FIG. 2.

Figure 3:
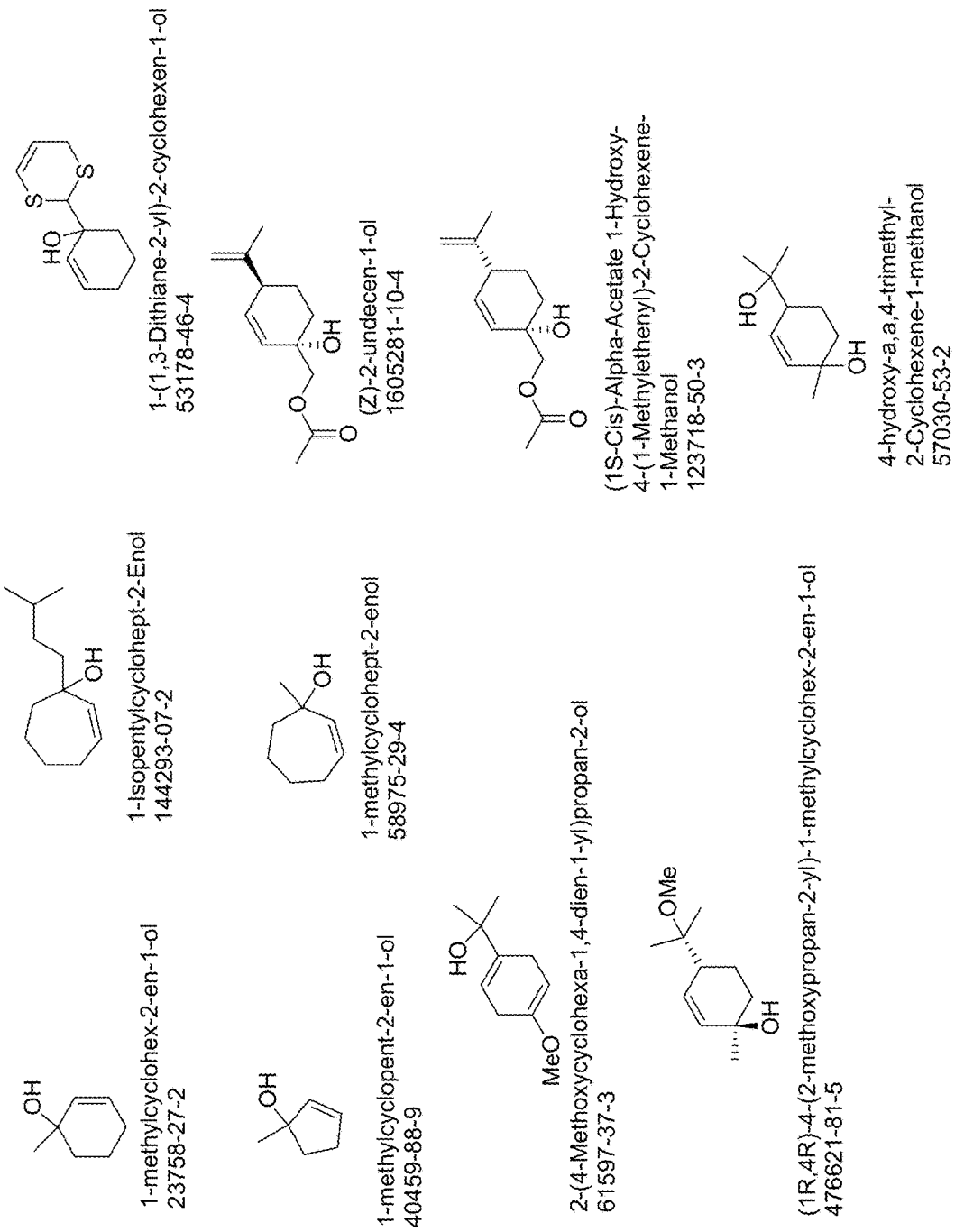
FIG. 3 Allylic alcohol reaction partners according to some embodiments and their CAS numbers.
Figure 3:
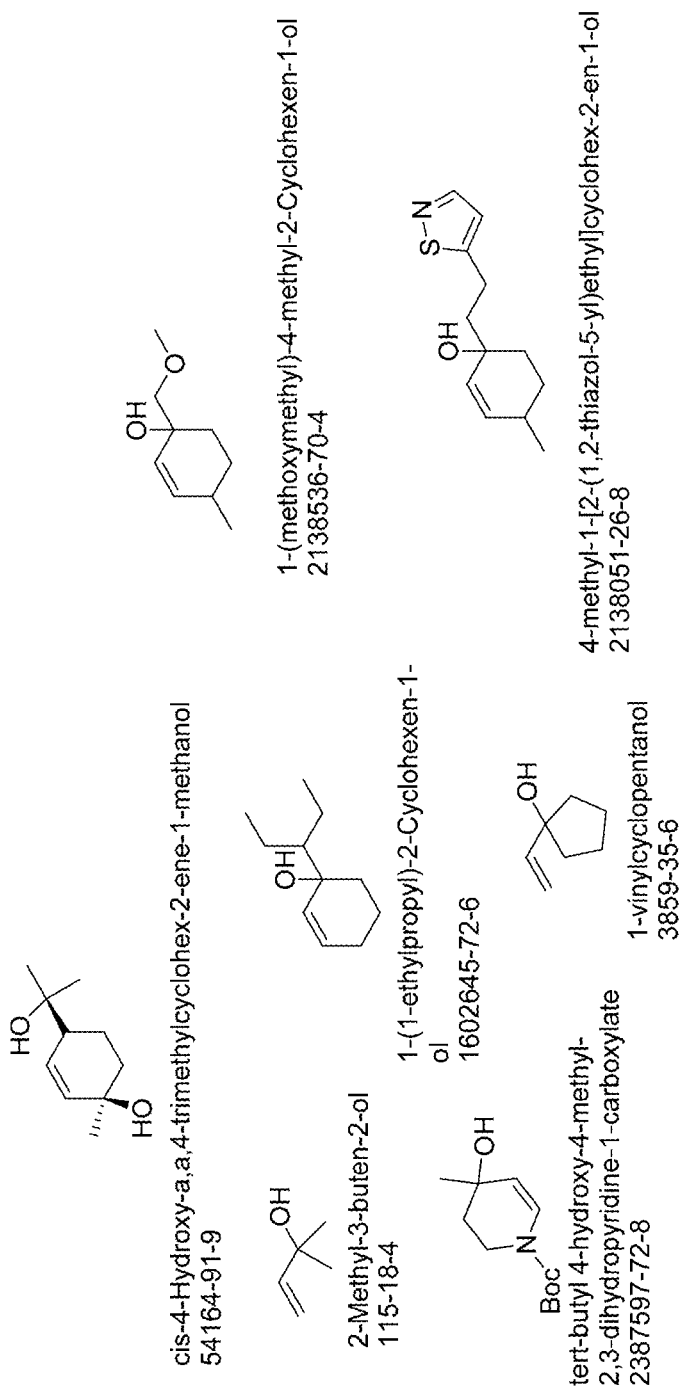

Candidate reagents for compound (IIIA), (IIIB), and (IIID) include but are not limited to allylic terpenols such as linalool, carveol, cis-verbenol, and other ionizable allylic alcohols such as cyclohex-2-enol, 1-vinylcyclohexanol, 1-methyl-2-cyclohexen-1-ol, and 1-methyl-2-cyclohepten-1-ol. Additional examples of allylic alcohol reaction partners according to some embodiments include but are not limited to 1-methylcyclohex-2-en-1-ol, 1-isopentylcyclohept-2-enol, 1-(1,3-dithiane-2-yl)-2-cyclohexen-1-ol, 1-methylcyclopent-2-en-1-ol, 1-methylcyclohept-2-enol, (Z)-2-undecen-1-ol, 2-(4-methoxycyclohexa-1,4-dien-1-yl)propan-2-ol, (1S-cis)-alpha-acetate 1-hydroxy-4-(1-methylethenyl)-2-cyclohexene-1-methanol, (1R,4R)-4-(2-methoxypropan-2-yl)-1-methylcyclohex-2-en-1-ol, 4-hydroxy-a,a,4-trimethyl-2-cyclohexene-1-methanol, cis-4-hydroxy-α,α,4-trimethylcyclohex-2-ene-1-methanol, 2-methyl-3-buten-2-ol, 1-(1-ethylpropyl)-2-cyclohexen-1-ol, tert-butyl 4-hydroxy-4-methyl-2,3-dihydropyridine-1-carboxylate, 1-vinylcyclopentanol, 4-methyl-1-[2-(1,2-thiazol-5-yl)ethyl]cyclohex-2-en-1-ol, and the allylic ethers derived thereof. The structures and CAS numbers of these representative allylic alcohols are shown by FIG. 3.

In some embodiments, compound (IA) is CBD ((−)-cannabidiol) or another isomer of CBD such as (+)-CBD, (−)-Δ6-CBD, or (+)-Δ6-CBD. In some embodiments, compound (I) is a homolog such as cannabidiphorol (CBDP) having a seven atom (heptyl) side chain. In some embodiments compound (I) is a hydrogenated CBD derivative such as 8,9-dihydroCBD. In some embodiments compound (I) is abnormal CBD (abn-CBD) or abnormal dihydroCBD (abn-H$_2$CBD).

In some embodiments compound (IA) is another cannabinoid such as cannabigerol (CBG) or cannabigerolic acid. In some embodiments, CBD or a CBD derivative (1A)-(1F) is a precursor to another cannabinoid such as cannabichromene (CBC), cannabinol (CBN), cannabielsoin (CBE), cannnabicyclol (CBL), cannabicitran (CBT), their isomers or derived analogues. In some embodiments, the CBD or CBD derivative compound (1A)-(1F) is a precursor to tetrahydrocannabinoid (THC) or isomers and analogues of THC such as (−)-Δ9-THC, (+)-Δ9-THC, (−)-Δ8-THC, and (+)-Δ8-THC. For example, compound (1A)-(1F) in some embodiments is a precursor and can be transformed to another cannabinoid, for example, through cyclization after formation of (1A)-(1F).

Figure 4:
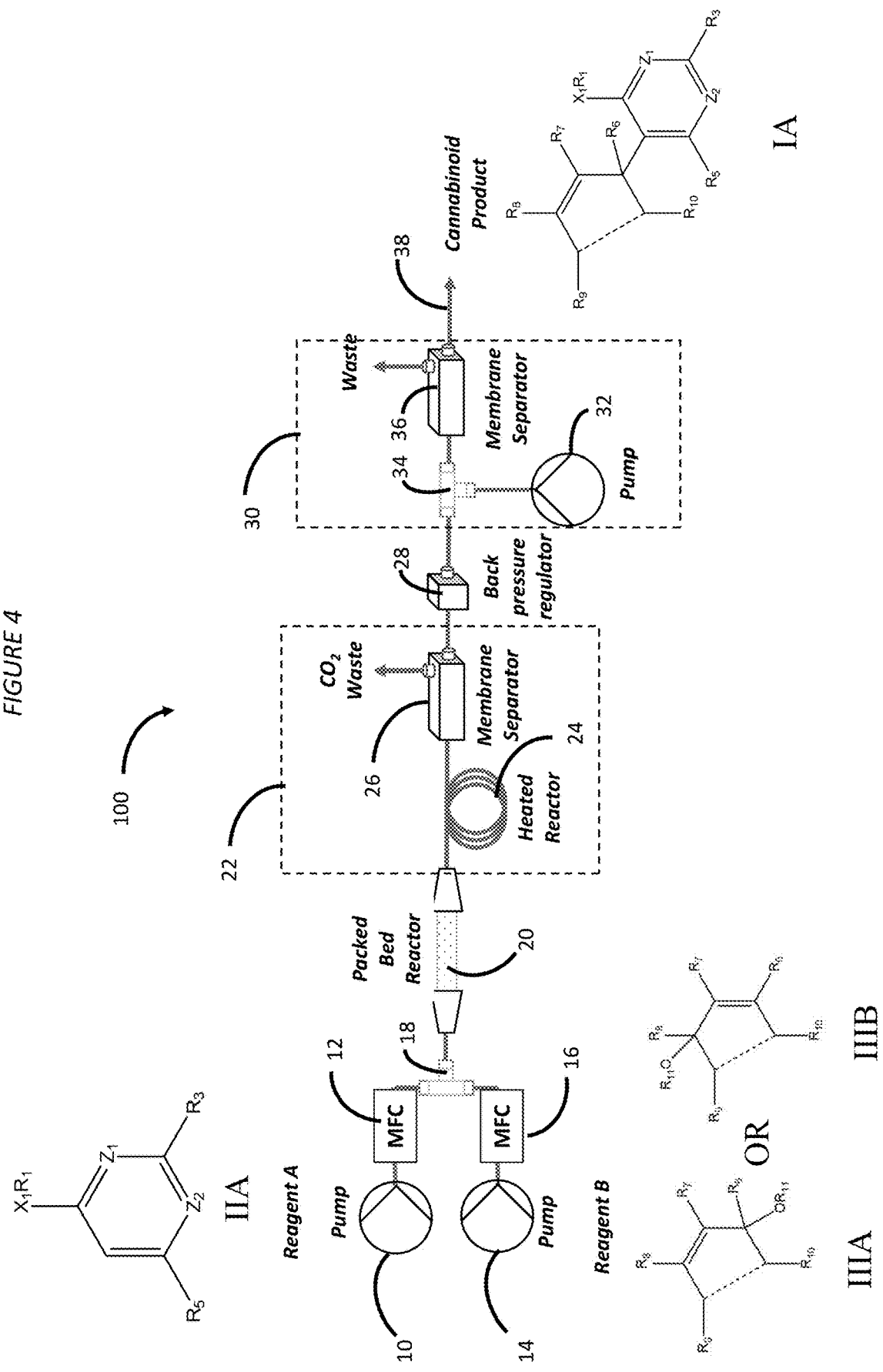
FIG. 4 shows a modular flow chemistry assembly line for the general production of cannabinoids using diverse aromatic compounds and oxygenated species such as allylic alcohols, esters, and carbonates.

Some embodiments of the continuous flow synthesis process are illustrated in FIG. 4, showing a modular flow chemistry assembly line system 100 for the production of cannabinoids, such as cannabinoid products (IA)-(IF), using diverse aromatic compounds (reagent A) and allylic alcohols/ethers/esters (reagent B). Reagent A can include compounds having the Formula (IIA) or (IIB) while reagent B can be compounds having Formula (IIIA)-(IIIE) Reagent A is pumped using a first pump 10 through a first mass flow controller (MFC) 12, and reagent B is pumped using a second pump 14 through a second mass flow controller 16 wherein the reagents are combined at T-junction 18. The combined reagents then are circulated through a packed bed reactor (PBR) 20 where they react. From the packed bed reactor, the products are optionally passed through an optional decarboxylation unit 22 outlined with a dotted line. The optional decarboxylation unit 22 includes the heated reactor 24 for thermolysis, for example, using temperatures in the range of 80 and 250 degrees Celsius (e.g. typically between 100 and 150 degrees Celsius). After heating, the products are passed through a separator 26 such as a membrane separator which separates $CO_2$ waste from the product stream. After passing through a back pressure regulator 28, the product stream is collected and isolated. Optionally, an aqueous addition unit 30 is used as indicated by the dotted lines. The aqueous addition subunit 30 includes a third pump 32 for addition of an aqueous solution to the product stream through a T-junction 34. The optional aqueous addition unit 30 includes a separator 36 such as a membrane separator to separate an aqueous stream from the organic stream containing the products. The product stream exits the assembly 100 as indicated by arrow 38 where it can be collected and further processed. In some embodiments the product stream is collected in a collection vessel.

Any of the regents and products as described herein can be used in the embodiments of the flow through reactor depicted by FIG. 4. For example, the reagents shown in Schemes 1-5 can be used to produce the corresponding CBD or CBD derivatives shown by these Schemes.

The asscembly system 100 can be made at any scale to produce multigram, multi-kilogram, or greater amounts of cannabinoid material per day. For example, the process using 100 can provide flow through rates of between about 0.1 mL/min and 100 L/min (e.g. between 0.1 mL/min-1 L/min). In some embodiments, the processes provide cannabinoids at the scale of greater than 1 kg (e.g. 10-100 Kg) per day.

In embodiments using a solvent to dissolve the reagents, the solvents can be independently selected from any inert solvent. For example, organic solvents can be selected from methylene chloride, dichloroethane, THF, methyl-THF, ethyl acetate, acetonitrile, hexanes, dioxane, trifluoromethyl benzene, and supercritical $CO_2$. An inert solvent is a solvent that does not react with the reagents starting materials or products and also does not react with or contaminate the catalyst. For example, some solvents having hydroxyl groups can compete for catalyst sites with starting regents that include hydroxyl groups, either by reacting to afford unwanted side products or blocking the desired reaction by contaminating the catalyst. Some catalysts are incompatible with water or oxygen and in these embodiments solvents that are hard to dry or deoxygenate can be avoided. Other solvents such as sulfur-containing solvents (e.g. dimethyl sulfoxide) can contaminate or deactivate catalysts and can be avoided in some embodiments.

In some embodiments where decarboxylation is desired, decarboxylation is done using continuous flow thermolysis. This system can include a heated tube reactor having a long path, such as a coiled tube as depicted by 24 (FIG. 4), that increases residence time and allows the product stream to be heated for enough time to decarboxylate the compounds in the reactor at the selected temperature. In some embodiments, flash thermolysis, where the product stream is rapidly heated to a high temperature, is used to rapidly decarboxylate the compounds. In some embodiments, decarboxylation is not desired or necessary because the final desired target product is as the acid form, or non-acid forms of starting materials are used.

As used herein a "packed-bed reactor" or "PBR" is an enclosure having an inlet and outlet, and containing a catalyst such as a solid supported or heterogeneous catalyst. As used herein, "circulating" solutions comprising compounds through the PBR refers to reagents such as A, B, and solvents, entering the PBR though the inlet, contacting the catalyst in the PBR, and then exiting the PBR though the outlet after the reagents have reacted. The reagents have a residence time controlled by flow rate (e.g., volume/time) and flow path length through the PBR (from the inlet to the outlet). In some embodiments, the PBR is in the form of an elongated enclosure such as a tube or column. For example, in some embodiments the tube or column can have an aspect ratio (diameter to length) of at least about 2, such as at least 5 (e.g. at least about 10, at least about 20, at least about 50, at least about 100). In some embodiments, the PBR is constructed using corrosive resistant materials such as stainless steel. In some embodiments, the PBR columns are designed to withstand pressures between about 1 psi (0.068 bar) and 5000 psi (345 bar). In some embodiments, the columns are designed and configured to provide interior temperatures between about −30 and 350° C. Accordingly, the PBR can include heating and cooling elements, such heating and cooling jackets, placement in a cooling (refrigerator) or heating (oven) enclosure. In some embodiments, the PBR includes pressure control and safety release valves and pressure control systems.

In some embodiments, the PCR is configured to be regenerated. For example, the catalyst after some use can become contaminated "fouled" or "poisoned" and can lose its effectiveness. Regeneration can include heating the PCR while flowing an inert (e.g. helium, nitrogen or argon), or active (e.g. hydrogen) through the PCR. Regeneration can also include heating and placing the PCR and catalyst under vacuum.

In some embodiments, the entire system pressure can be maintained by a membrane back pressure regulator, such as back pressure regulator 28. In some embodiments a back pressure regulator is inserted between units in the modular flow chemistry assembly line 100, for example between a decarboxylation unit 22 and an aqueous addition unit 30. In some embodiments more than one back pressure regulator is used, for example to provide controlled and different pressures to different units within the assembly line 100. In some embodiments, commercial back pressure regulators such as those available from Zaiput Flow Technologies (MA, USA) are used.

In some embodiments, the PBR is constructed as a series of enclosures, such as a series of connected columns, where the outlet from one column can be connected to the inlet of the next column in the series. Between the columns containing catalysts, the connection can optionally be made using a tube not including catalyst. In some embodiments, the PBR is constructed as parallel enclosures, for example where the inlets of two or more columns are connected and the outlets of the two or more columns are also connected. In some embodiments, the outlet to the PBR is connected to the inlet or any position between the inlet and the outlet of the PBR. For example, the connection can be controlled to return the material in the outlet from the PBR back into the PBR. This provides a method to extend the residence time of contact between the reagents and catalyst in the PBR, for example, if needed to progress the reaction towards completion. It is contemplated that such connections would include flow control valves so that precise control of flow can be achieved, e.g. to direct flow back into or out of the PBR.

In some embodiments, the PBR includes catalysts housed in columns e.g. stainless steel columns. In some embodiments, commercially available components such as Kinesis Omnifit® (10 mm×150 mm) columns (Kinesis Ltd.) can be used, for example for the gram scale preparation of cannabinoids. In some embodiments, custom-in house packed bed (30 mm×300 mm) columns are used for the kilogram and larger scale synthesis of cannabinoids.

In some embodiments, the packed bed reactor 20 contains a solid or heterogeneous acid catalyst. Without limitation, these solid or heterogamous catalysts have a high surface area and internal structure or pores the reagents can access. For example, catalysts having accessible surfaces between about 1 $m^2/g$ to 7000 1 $m^2/g$ (e.g., about 10 to about 1000 1 $m^2/g$) can be used in typical embodiments.

In some embodiments, solid acid catalysts that can be used include but are not limited to acidic large-pore (e.g. greater than about 50 nm diameter average pour size) and medium-pore (e.g. between about 10 and 50 nm diameter average pour size) zeolites (e.g. Zeolite HY and Y0), aluminosilicates such as Montmorillonite K10 or KSF clay, Nafion-NR50, sulfated zirconia, silica gel, polyaniline sulfate, graphene oxide (GO) and carboxylic acid functionalized GO (GO-$CO_2$H), polymer-supported boronic acids, heteropolyacids, tungstated zirconia, and heterogeneous sulfonic acids. In some embodiments the heterogeneous sulfonic acids include amorphous carbon-bearing supported sulfonic acids, sulfonic acid-functionalized mesoporous silica (SBA-Pr—$SO_3$H), boron sulfonic acid, sulfated tin oxide, and polystyrene-supported sulfonic acid resins (both gel type and macroporous) such as Amberlyst-15 and macroporous-TsOH (MP-TsOH). In some embodiment of the catalyst includes β-cyclodextrin-butane sulfonic acid, β-cyclodextrin-propyl sulfonic acid, or β-cyclodextrin on a resin, such as β-cyclodextrin on Dowex resin. In some embodiments, the solid acid catalyst includes Lewis acids, such as Lewis acids used in liquid-phase reactions, that are supported on a surface. Without limitation, Lewis acids that can be used include $AlCl_3$, $BF_3$, $SnCl_4$, and $TiCl_4$. These Lewis acids can be supported on a high-surface-area solid such as graphite, alumina ($Al_2O_3$) such as halogenated and non-halogenated alumina, mesoporous silicates (e.g. MCM-41), high surface silica $SiO_2$ such as fumed silica, aluminosilicates, magnesium silicates (e.g. talc), zeolites, and clays. In some embodiments, chlorinated or fluorinated alumina ($Al_2O_3$) or $AlCl_3$ which is immobilized on mesoporous MCM-41 silica can be used. In some embodiments the Lewis acid catalysts are β-alumina trifluoride, alumina chlorofluoride and aluminas γ and η with partially fluorinated or chlorinated surfaces. In some embodiments, β-cyclodextrin is modified by reaction with a sultone (e.g. pentane, propane, and propane sultone) in the presence of base (e.g. NaOH) providing a sulfo-alkyl ether-β-cyclodextrin. In some embodiments, the sulfo-alkyl ether-β-cyclodextrin can be attached to a surface to provide a heterogenized acid catalyst having the hydrophobic-β-cyclodextrin cavity for accepting reagents, and the acid sulfonic acid group. Optionally, protic acids on solid supports can be used such as perchloric acid immobilized on silica gel ($HClO_4$—$SiO_2$) or fluoroboric acid immobilized on silica gel ($HBF_4$—$SiO_2$). Optionally, the supported catalyst can be comprised of a sulfonic acid-substituted calix[x]arene derivative supported on polystyrene, silica, controlled pore glass, or other solid support. Optionally the substituted calix[x]arene comprises calix[8] arene sulfonic acid, calix[6]arene sulfonic acid, or calix[4] arene sulfonic acid.

Some of the compounds disclosed herein can exist in various isomeric forms, such as regioisomers and stereoisomers. Regioisomers are compounds where the basic carbon skeleton, such as the aromatic ring of CBD, remains unchanged but functional groups, such as the —$C_5H_{11}$ alkyl group in CBD are in a different position on the aromatic ring relative to the hydroxyl groups. Stereoisomers are compounds that differ only in their spatial arrangement. Enantiomers are pairs of stereoisomers whose mirror images are not superimposable, most commonly because they contain an asymmetrically-substituted carbon atom that acts as a chiral center. "Enantiomer" means one of a pair of molecules that are mirror images of each other and are not superimposable. Diastereomers are stereoisomers that contain two or more asymmetrically substituted carbon atoms. "R" and "S" represent the configuration of substituents around one or more chiral carbon atom.

Some embodiments of the continuous flow through process provide compounds as individual enantiomers by either directly, wherein the process is enantiospecific, or are resolved from an enantiomerically enriched mixture. When the stereochemistry of a disclosed compound is named or depicted, the named or depicted stereoisomer can be at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

In another embodiment, the present disclosure can produce the compounds of interest, such as CBD, in high stereospecificity (e.g. either (−)-CBD or (+)-CBD), in a one-step flow mediated process. As used herein "high stereospecificity" means that the processes of the present disclosure can provide the target product with enantioselectivity greater than about 60% ee, 75% ee, 80% ee, 85% ee, 90% ee, 95% ee, 97% ee, 98% ee, or 99% ee. These values can define a range, such as about 90% ee and about 99% ee.

In some embodiments, the present disclosure can produce the compounds of interest, such as CBD, in high yield and regiospecificity. As used herein, a high yield is greater than 70% product yield of all isomers based on the limiting reagent (e.g. greater than 80%, greater than 90%, greater than 99%). As used herein, having a high regioselectivity means that in the product mixture, including all regioisomers before any isolation or purification, at least 50 mol % of the product is one regioisomer, such as the regioisomer having the structures of (IA)-(IF), (e.g. at least 60 mol. %, at least 70 mol. %, at least 80 mol. %, at least 90 mol.%, at least 99 mol. %).

In some embodiments, the present disclosure can produce the compounds of interest, such as CBD, in high yield of one regioisomer and in high stereospecificity, for example, the CBD derivative depicted by structure (V).

Without being bound to any specific theory, it is proposed that the heterogeneous catalysts provide surfaces and pores for adsorption and activation of the reagents wherein regiospecific and stereospecific reaction to product (IA)-(IF) is enforced or favored, over other possible regioisomers and stereoisomers, in high yields. For example, the regioselectivity and steroselectivity is high even without the use of any blocking or activating groups, e.g. such as where groups $R_2$ and $R_4$ in (IIA)-(IIB) are not halides.

In some embodiments, the product stream is isolated or purified. As used herein to "purify" or "isolate", is any step that increases the concentration of the target product, e.g. the target cannabinoid, or any step that increases the ratio of the target product relative to non-target products (e.g. non-target reaction products or impurities). For example, after the isolation step or process, the concentration of the desired product such as any one of (IA)-(IF) in the product stream is higher than before the isolation step, or the molar ratio of the desired product to any other compound in the product stream is higher than before the isolation step.

In some embodiments, the product stream includes two or more desired products efficiently and in a high total yield wherein the products are easy to separate. For example, normal and abnormal cannabinoids, such as normal CBD and abnormal CBD. In some embodiments the products are not separated and provide synergistic benefits.

In some embodiments, the methods for isolation can include a continuous methods integrated with system 100. For example, in some embodiments the product stream is combined with a solution that forms a two phase solution. Overall, the product is diluted in relation to the total volume of both phases, but the solutions (e.g. organic solvent and aqueous solution) can be selected where the desired product (IA)-(IF) has a higher solubility in one of the phases. In some embodiments the reagents (e.g., IIA-IIB, IIIA-IIIE) are combined with an organic solvent to circulate through PBR 20, and unit 30 dilutes the product stream with an aqueous solution. The Product (e.g., IA-IF), having higher solubility in the organic phase, will concentrate in the organic phase. After separation, the product stream includes only the organic phase having the product. The aqueous phase includes more polar compounds such as salts and highly oxidized compounds as well as, in some embodiments, any unreacted starting reagents. Without limitation, the aqueous phase can include salts (e.g. sodium, potassium and ammonium salts) or surfactants (e.g. anti-foam agents) to improve the separation of (I) from other molecules and handling of the solution (e.g. avoiding emulsification).

Without limitation, in some embodiments separations of two phases, such as an aqueous phase and an organic phase, or a gas phase and a liquid phase, can use a membrane separator. As used herein a membrane separator includes a porous membrane that contacts the mixture to be separated, wherein the pores are dimensioned to selectively allow permeation of either the desired component, or to retain the desired component. For example, a $CO_2$ membrane separator can include a membrane that allows passage of $CO_2$ gas while retaining larger solvents and molecules such as products (IA)-(IF) in solution. As another example, in some embodiments water purification methods such as reverse osmosis membrane separation where pressure is applied against a mixture of an organic and aqueous phase in a membrane separator 36 to force the water through a semipermeable membrane and separate water molecules from the organic phase constituents within the water. In some embodiments, the membrane separator is used to separate an aqueous phase that has been added to the product stream, for example by unit 30. In some other embodiments, a membrane separator is used even though unit 30 is not used. For example, any water or other small molecule such as methanol that is produced or liberated in the PBR during reaction of the reagents, or can be present within the solvents, can be removed from the product stream. In some embodiments commercial separators such as membrane separators for water separation available from Zaiput Flow Technologies (MA, USA) are used.

In some embodiments, the isolation or purification step is a process that is a batch process. For example, in some embodiments the product stream 38 is directed to a tank or container that can collect the product stream, providing a collected product stream. The product can then be isolated from the collected product stream. In some embodiments the collected product stream is mixed with an aqueous solution and the organic phase with high concentration of the desired product such as (IA)-(IF) is isolate from the aqueous phase. For example, the separation can be as previously described using a membrane separator, or can be by simply letting the phases separate and decanting the desired organic phase from the aqueous phase. In some embodiments the product stream does not include an aqueous phase.

In some embodiments, the product stream or collected product stream can be concentrated, for example, by applying heat and/or vacuum. For example, in some embodiments a rotary evaporator is used to remove solvents. In some embodiments, the product stream is collected or directly fed to a thin film or wiped film evaporator to remove solvents and provide a concentrated product.

In some embodiments, the product stream or collected product stream is distilled, to remove solvents and any side products or impurities. Distillation can be under vacuum or at atmospheric pressure. In some embodiments, the heating during distillation also decarboxylates the product, for example, where the starting reagents compounds (IIA)-(IIB) include a carboxylic acid and the decarboxylation unit 30 is not included, or is only partially effective for decarboxylation. In some embodiments the collected product stream is heated to decarboxylate the product, e.g. where the solvent is removed and the product is heated optionally under vacuum (e.g. using a vacuum oven).

In some embodiments, the product is crystalized or precipitated from the collected product stream. For example, a super-saturated solution containing the products such as (IA)-(IF) can be made by evaporation of solvents, adding a second solvent that is miscible with the solvent of the product stream but has a lower solubility for the product or by cooling and allowing crystal or precipitate formation.

In some embodiments, the product stream or collected product stream is filtered. For example, a filter can be used to collect precipitated or crystalized product. Filtering can also be used to remove any unwanted compounds such as insoluble materials e.g., oligomers, polymers, and salts.

In some embodiments, the product stream is contacted with a high surface material to remove an impurity, such as a colored impurity. For example, the product stream can be contacted with a high surface material that adsorbs colored impurities, such as active carbon. The adsorbing material can be packing in a column and the product stream can be made to flow through the adsorbing material, or the active material can be slurred with the collected product stream and then filtered away from product containing solutions.

In some embodiments the product stream or a collected product stream is purified using a chromatographic method. For example, a packed column or silica gel or other separation medium. Optionally, the chromatographic method is a continuous method such as Simulated Moving Bed (SMB) chromatography. For example, commercially available SMB systems can be used such as those available from Semba Biosciences Inc., (WI) and Purist LLC include systems that can process 200 mL/min flow rates and output 1 kg of cannabinoid product per day.

In some embodiments, the product stream or collected product stream is dried. For example, by contacting the product stream or collected product stream with drying materials such as drying sieves or anhydrous magnesium sulfate. In some embodiments the product is spray dried. For example, producing a dry, free flowing, powder with controlled particle size from the product stream by aerosolizing the material by spraying through a nozzle into and optionally heated environment where the solvents/water evaporate and the dry powder can be collected. In some embodiments, drying is by applying vacuum or heat to the product stream.

In some embodiments, more than one isolation and purification method can be used. For example, the product stream can be subjection to a phase separation between an aqueous (waste) phase and organic product stream, the organic product stream can be collected and then concentrated (e.g. by rotary evaporation), and then product such as (IA)-(IF) can be crystalized from the concentrated collected product stream, or the product can be distilled (e.g. by fractional distillation) from the concentrated collected product stream.

In some embodiments, one or more component for the modular flow chemistry assembly line 100 are commercially available. For example, commercially available components and systems can be purchased from Fluitec Mixing+Reaction Solution (Germany). Without limitation, one or more components can be purchased or can be made (e.g. designed and made in house) and assembled into the assembly 100. For example, one or more of the fluid bed reactors, the pumps, the tubing, the MFCs, the membrane separators, the heaters, and the membrane separators can be either purchased or designed/made in house.

Figure 5:
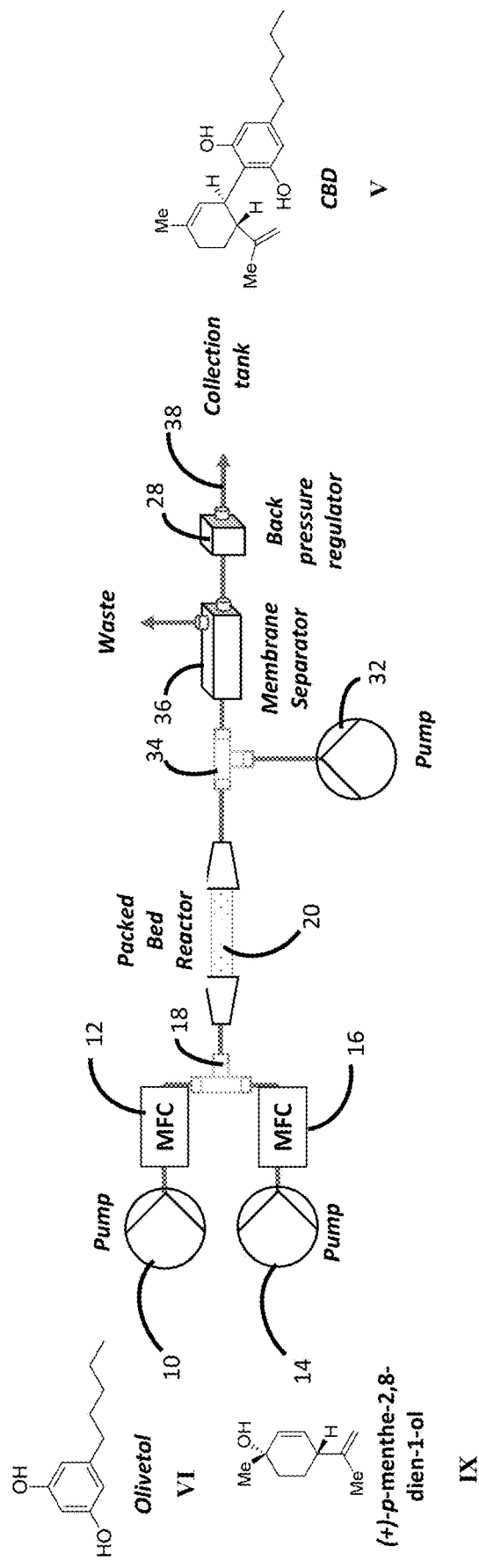
FIG. 5 shows a modular flow chemistry assembly line for CBD production.

FIG. 5 shows an embodiment for preparation of CBD (V) by the reaction of olivetol (VI) with (+)-p-mentha-2,8-dien-1-ol (IX). Solutions of reagents (VI) and (IX) are moved by gear pumps 10 and 12 (0.1 mL/min-25 mL/min, Valco Instruments M Series Pumps) which are metered via feedback from mass flow controllers 12 and 16 (Brooks Instruments, Coriolis). Solvents for dissolving the key reagents include without limitation methylene chloride, dichloroethane, THF, methyl THF, ethyl acetate, acetonitrile, hexanes, dioxane, trifluoromethyl benzene, and supercritical $CO_2$. The reagent solutions are combined at a T-union 18 and then travel into a PBR 20 which contains a solid acid catalyst. After optimization of flow rate and completion of the reaction, the solution is diluted at a T-union 34 with an aqueous stream which is introduced using gear pump 32. The biphasic solution passes through a membrane separator 36 (Zaiput Flow Technologies) at which point the aqueous solution is collected as waste and the organic solution 38 containing CBD enters into a collection tank and is prepared for crystallization. At room temperature, CBD is a colorless, crystalline solid. The entire system pressure is maintained by a membrane back pressure regulator 28 (Zaiput Flow Technologies). Any of the reagents, such as those shown in Schemes 1-5 can be used with the system shown by FIG. 5, to provide the corresponding CBD or CBD derivative.

Figure 6:
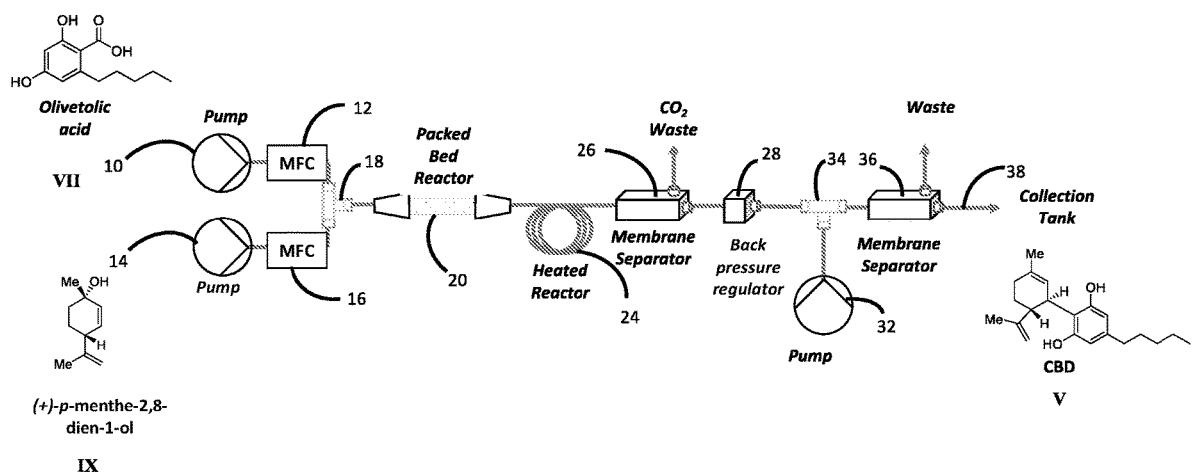
FIG. 6 shows another modular, flow chemistry assembly line for CBD production.

A further embodiment is shown schematically in FIG. 6. Substrate solutions of olivetolic acid (VII) and (+)-p-menthe-2,8-dien-1-ol (IX) are moved by gear pumps 12 and 16 (0.1 mL/min-25 mL/min Valco Instruments M Series Pumps) which are metered via feedback from mass flow controllers 12 and 16 (Brooks Instruments, Coriolis). The solutions are combined at a T-union 18 and travel into a PBR 20 (Kinesis Omnifit) which contains a solid acid catalyst. After the reaction is complete, the solution is moved into a heated reaction chamber 24 which facilitates decarboxylation. The generated carbon dioxide gas is removed using a membrane separator 26 (Zaiput Flow Technologies) and the solution containing CBD is diluted at a T-union 34 with an aqueous stream which is introduced using a gear pump 12. The biphasic solution passes through a second membrane separator 36 (Zaiput Flow Technologies) at which point the aqueous solution is collected as waste and the organic solution, containing CBD, enters into the collection tank and prepared for crystallization. The entire system pressure is maintained by a membrane back pressure regulator (Zaiput Flow Technologies). Other 2,4-dihydroxybenzoic acids ((β-resorcylic acids) can also be used in this embodiment to produce targeted CBD analogues. Any of the reagents, such as those shown in Schemes 1-5 can be used with the system shown by FIG. 6, to provide CBD or the corresponding CBD derivative.

Some embodiments further comprise pharmaceutical compositions containing a therapeutically effective amount of a compound prepared according to any of the processes described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier can take a wide variety of forms depending upon the desired route of administration (e.g. oral, parenteral). Thus, for liquid oral preparations such as suspensions, elixirs, and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations can also be coated with substances such as sugars or be enteric-coated so as to modulate major site of absorption. For parenteral administration, the carrier will usually consist of sterile water and other ingredients can be added to increase solubility or preservation. Injectable suspensions or solutions can also be prepared utilizing aqueous carriers along with appropriate additives.

To prepare the pharmaceutical compositions according to some embodiments, one or more compounds described herein as the active ingredient is intimately admixed with a pharmaceutical carrier according to conventional pharmaceutical compounding techniques, which carrier can take a wide variety of forms depending of the form of preparation desired for administration, e.g. oral or parenteral such as intramuscular. In preparing the compositions in oral dosage form, any of the usual pharmaceutical media can be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets can be sugar coated or enteric coated by standard techniques. For parenteral administration, the carrier will usually comprise sterile water, through other ingredients, for example, for purposes such as aiding solubility or for preservation, can be included. Injectable suspensions can also be prepared, in which case appropriate liquid carriers, suspending agents and the like can be employed. The pharmaceutical compositions herein will contain, per dosage unit, e.g. tablet, capsule, powder, injection, teaspoonful, and the like, an amount of the active ingredient necessary to deliver an effective dose as described above. The pharmaceutical compositions herein will contain, per unit dosage unit, e.g. tablet, capsule, powder, injection, suppository, teaspoonful, and the like, of from about 0.01 mg to about 1000) mg or any amount or range therein, and can be given at a dosage of from about 0.01 mg/kg/day to about 300 mg/kg/day, or any amount or range therein, for example from about 0.1 mg/kg/day to about 50 mg/kg/day, or any amount or range therein, or for example from about 0.05 mg/kg/day to about 15 mg/kg/day, or any amount or range therein. In some embodiments a recommended starting dosage is from 5 mg/kg/day to about 20 mg/kg/day, or any amount or range therein. In some embodiments the dosage is administered over several smaller dosages, for example a 5 mg/kg/day can be administered in two dosages of 2.5 mg/kg approximately every 12 hours (e.g. 8 am and 8 pm). The dosages, can be varied depending upon the requirement of the patients, the severity of the condition being treated and the compound being employed. The use of either daily administration or post-periodic dosing can be employed.

In some embodiments, these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition can be presented in a form suitable for once-weekly or once-monthly administration; for example, an insoluble salt of the active compound, such as the decanoate salt, can be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the invention, or a pharmaceutically acceptable salt thereof. When referring to these preformulation compositions as homogeneous, it is meant that the active ingredient is dispersed evenly throughout the composition so that the composition can be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the invention. In one embodiment, the solid preformulation composition is subdivided into unit dosage forms containing from about 0.01 mg to about 0.1 mg. In another embodiment, the solid preformulation composition is subdivided into unit dosage forms containing from about 0.05 mg to about 0.5 mg. In another embodiment, the solid preformulation composition is subdivided into unit dosage forms containing from about 0.1 mg to about 1 mg. In another embodiment, the solid preformulation composition is subdivided into unit dosage forms containing from about 0.5 mg to about 5 mg. In another embodiment, the solid preformulation composition is subdivided into unit dosage forms containing from about 1 mg to about 10 mg. In another embodiment, the solid preformulation composition is subdivided into unit dosage forms containing from about 5 mg to about 50 mg. In another embodiment, the solid preformulation composition is subdivided into unit dosage forms containing from about 10 mg to about 100 mg. In another embodiment, the solid preformulation composition is subdivided into unit dosage forms containing from about 50 mg to about 500 mg. In another embodiment, the solid preformulation composition is subdivided into unit dosage forms containing from about 250 mg to about 750 mg. In another embodiment, the solid preformulation composition is subdivided into unit dosage forms containing from about 500 mg to about 1000 mg.

The tablets or pills of the composition according to some embodiments can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol, and cellulose acetate.

The liquid forms in which the compositions can be incorporated for administration orally or by injection include, aqueous solutions, suitably flavored syrups, aqueous or oil suspensions, and flavored emulsions with edible oils such as cottonseed oil, hemp seed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, or gelatin.

Some embodiments include a method of treating pain, anxiety, sleep disorders, Lennox-Gastaut and Dravet syndromes, and other indications. These methods can be carried out using a pharmaceutical composition including a therapeutically effective amount of any of the compounds as defined herein and a pharmaceutically acceptable carrier. The pharmaceutical composition can contain between about 0.01 mg and about 1000 mg of the compound, or any amount or range therein, preferably from about 1.0 mg to about 500 mg of the compound, or any amount or range therein, and can be constituted into any form suitable for the mode of administration selected. In one embodiment, the pharmaceutical composition contains between about 0.01 mg and about 1 mg of the compound. In another embodiment, the pharmaceutical composition contains between about 0.05 mg and about 5 mg of the compound. In another embodiment, the pharmaceutical composition contains between about 2.5 mg and about 10 mg of the compound. In another embodiment, the pharmaceutical composition contains between about 5 mg and about 25 mg of the compound. In another embodiment, the pharmaceutical composition contains between about 15 mg and about 50 mg of the compound. In another embodiment, the pharmaceutical composition contains between about 25 mg and about 75 mg of the compound. In another embodiment, the pharmaceutical composition contains between about 50 mg and about 100 mg of the compound. In another embodiment, the pharmaceutical composition contains between about 75 mg and about 250 mg of the compound. In another embodiment, the pharmaceutical composition contains between about 125 mg and about 500 mg of the compound. In another embodiment, the pharmaceutical composition contains between about 300 mg and about 750 mg of the compound. In another embodiment, the pharmaceutical composition contains between about 650 mg and about 1000 mg of the compound.

In some embodiments, carriers can comprise inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

In some embodiments, the compounds of the invention can be administered in a single daily dose, or the total daily dosage can be administered in divided doses of two, three or four times daily. Furthermore, compounds for the invention can be administered in intranasal form via topical use of suitable intranasal vehicles, or via transdermal skin patches well known to those of ordinary skill in that art. To be administered in the form of a transdermal delivery system, the dosage administration will be continuous rather than intermittent throughout the dosage regimen For example, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum, and the like.

In some embodiments, the liquid forms include any suitably flavored suspending or dispersing agents such as synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition according to some embodiments, a compound prepared according to any of the processes described herein as the active ingredient is intimately admixed with a pharmaceutical carrier according to conventional pharmaceutical compounding techniques, which carrier can take a wide variety of forms depending of the form of preparation desired for administration (e.g. oral or parenteral). Suitable pharmaceutically acceptable carriers are well known in the art. Descriptions of some of these pharmaceutically acceptable carriers can be found in The Handbook of Pharmaceutical Excipients, published by the American Pharmaceutical Association and the Pharmaceutical Society of Great Britain, the entirety of which is incorporated herein by reference.

Methods of formulating pharmaceutical compositions have been described in numerous publications such as "Pharmaceutical Dosage Forms: Tablets", Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc., the entirety of which are incorporated herein by reference.

In some embodiments, the compounds described herein can be administered in any of the foregoing compositions and according to dosage regimens established in the art whenever treatment of pain, anxiety, sleep disorders, Lennox-Gastaut, Dravet syndromes, and other disorders is required. In some embodiments, the treatment is for a human adult, human child, or human infant. In some embodiments, the treatment is for a non-human. For example, in some embodiments the treatment is for a mammal such as a dog, cat, or horse.

The daily dosage of the products can be varied over a wide range, from about 0.01 mg to about 1,000 mg per day, or any amount or range therein. In one embodiment, the daily dosage of the products can be from about 0.01 mg to about 5 mg per day. In another embodiment, the daily dosage of the products can be from about 2.5 mg to about 10 mg per day. In another embodiment, the daily dosage of the products can be from about 5 mg to about 25 mg per day. In another embodiment, the daily dosage of the products can be from about 15 mg to about 50 mg per day. In another embodiment, the daily dosage of the products can be from about 25 mg to about 75 mg per day. In another embodiment, the daily dosage of the products can be from about 50 mg to about 100 mg per day. In another embodiment, the daily dosage of the products can be from about 75 mg to about 250 mg per day. In another embodiment, the daily dosage of the products can be from about 125 mg to about 500 mg per day. In another embodiment, the daily dosage of the products can be from about 350 mg to about 750 mg per day. In another embodiment, the daily dosage of the products can be from about 500 mg to about 1000 mg per day.

For oral administration, the compositions are preferably provided in the form of tablets containing, about 0.01 mg, about 0.05 mg, about 0.1 mg, about 0.5 mg, about 1.0 mg, about 2.5 mg, about 5.0 mg, about 10.0 mg, about 15.0 mg, about 25.0 mg, about 50.0 mg, about 100 mg, about 150 mg, about 200 mg, about 250 mg, and/or about 500 mg of the active ingredient for the symptomatic adjustment of the dosage to the patient to be treated. An effective amount of the drug is ordinarily supplied at a dosage level of from about 0.01 mg % kg to about 500 mg/kg of body weight per day, or any amount or range therein. In some embodiments, the range is from about 0.1 to about 50.0 mg/kg of body weight per day, or any amount or range therein. In some embodiments the dosage is from about 0.5 to about 15.0 mg/kg of body weight per day, or any amount or range therein. In some embodiments the dosage is from about 1.0 to about 7.5 mg/kg of body weight per day, or any amount or range therein. In some embodiments the dosage is from about 5 mg/kg/day to about 20 mg/kg/day or any amount or range therein. The compounds can be administered on a regimen of 1 to 4 times per day.

Optimal dosages to be administered can be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known, and generally accepted cell and/or animal models are predictive of the ability of a test compound to treat or prevent a given disorder.

One skilled in the art will further recognize that human clinical trials, including first-in-human, dose ranging, and efficacy trials, in healthy patients and/or those suffering from a given disorder, can be completed according to methods well known in the clinical and medical arts.

Embodiments of various aspects described herein can be defined as in any of the following numbered paragraphs:

1. A process for the preparation of a cannabidiol (CBD) or a derivative thereof, the process comprising:
   (a) providing a solution comprising of a first compound that is a 1,3-diene or an allylic alcohol or allylic ether and a second compound of Formula (IIA) or (IIB) into a packed-bed reactor (PBR) comprising a solid or heterogeneous catalyst;
   (b) flowing the first and second compound through the PBR to react the first compound with the second compound;
   (c) collecting the eluant solution from the PBR a solution comprising the CBD or a derivative thereof;
   wherein the structures of (IIA) and (IIA) are:

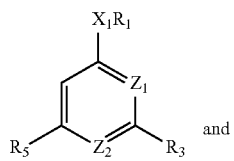

(IIA)

and

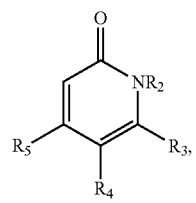

(IIB)

wherein: $Z_1$ is $CR_2$ or N and $Z_2$ is $CR_4$ or N;
wherein $R_1$, $R_3$, $R_5$, are each independently selected from the group consisting of H, OH, —$CO_2H$, protected hydroxyl, alkyl, alkenyl, alkynyl, acyl, aryl, heteroaryl, cycloalkyl, heterocycle, —$X_2R^K$, or halides,
wherein $R_2$, and $R_4$, are each independently selected from the group consisting of H, OH, —$CO_2H$, protected hydroxyl, alkyl, alkenyl, alkynyl, acyl, aryl, heteroaryl, cycloalkyl, heterocycle, —$X_2R^K$ and not selected from halides,
wherein the alkyl, alkenyl, alkynyl or acyl is optionally substituted with one or more substituents independently selected from the group consisting of halogen, —OH, alkyl, O-alkyl, —$NR^AR^B$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —$N(R^G)$— substituting one or more carbons in the carbon chain,
wherein the aryl or heteroaryl, whether alone or as part of a substituent group, is optionally substituted with one or more substituents independently selected from the group consisting of halogen, OH, alkyl, O-alkyl, —COOH, —C(O)—$C_{1-4}$ alkyl, —C(O)O—$C_{1-4}$ alkyl, —$NR^CR^D$, —S-alkyl, —SO-alkyl and —$SO_2$-alkyl;
wherein $X_1$ is selected from —O—, —S—, —$SO_2$—, —$N(R^E)$—;
wherein $X_2$ is selected from —O—, —S—, —$SO_2$—, —$N(R^F)$—;
wherein $R^A$, $R_B$, $R^C$, $R^D$, $R^E$, $R^F$, $R^K$ and $R^G$ are each independently selected from hydrogen and $C_{1-4}$ alkyl;
or a pharmaceutically acceptable salt or ester thereof.

2. The process according to paragraph 1, wherein the first compound has structure selected from the group consisting of:

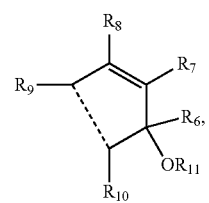

(IIIA)

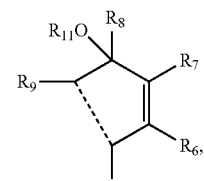

(IIIB)

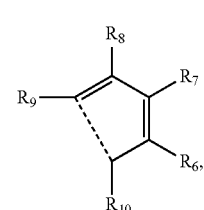

(IIIC)

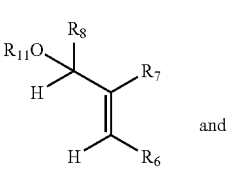

(IIID)

and

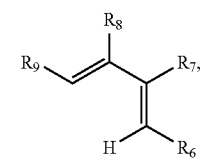

(IIIE)

wherein $R_6$, $R_7$, $R_8$, $R_9$, $R_{10}$ and $R_{11}$ are each independently selected from the group consisting of H, OH, —$CO_2H$, protected hydroxyl, alkyl, alkenyl, alkynyl, acyl, aryl, heteroaryl, cycloalkyl, heterocycle, —$X_2R^K$, or halides,
wherein the alkyl, alkenyl, alkynyl or acyl is optionally substituted with one or more substituents independently selected from the group consisting of halogen, —OH, alkyl, O-alkyl, —$NR^AR^B$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —$N(R^G)$— substituting one or more carbons in the carbon chain,
wherein $X_1$ is selected from —O—, —S—, —$SO_2$—, —$N(R^E)$—;
wherein $X_2$ is selected from —O—, —S—, —$SO_2$—, —$N(R^F)$—;
wherein -------- is absent or a $C_{1-3}$ alkylene linker, which links the carbon bonded to $R_9$ and the carbon bonded to $R_{10}$;
wherein $R^A$, $R_B$, $R^C$, $R^D$, $R^E$, $R^F$, $R^K$ and $R^G$ are each independently selected from hydrogen and $C_{1-4}$ alkyl;
or a pharmaceutically acceptable salt or ester thereof.

3. The process of paragraph 1 or 2, wherein the CBD or the derivative thereof has a structure selected from the group consisting of:

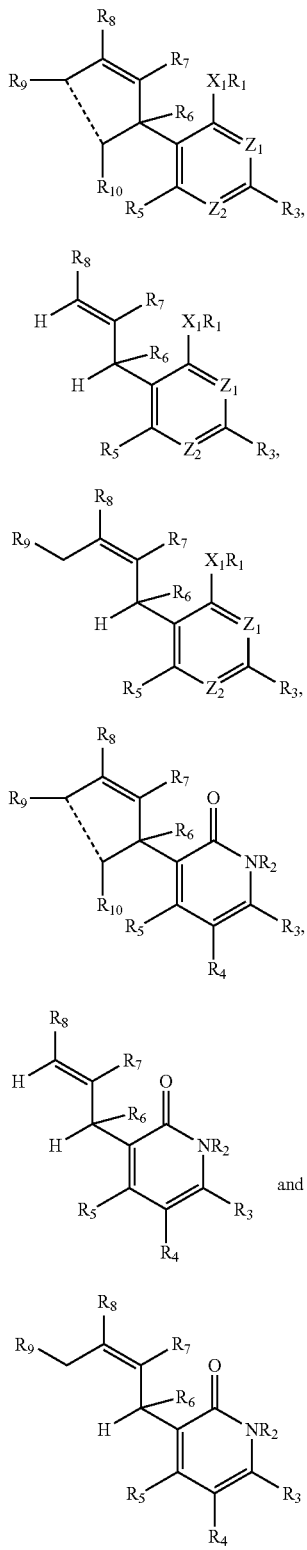

wherein $R_6$, $R_7$, $R_8$, $R_9$, and $R_{10}$ are each independently selected from the group consisting of H, OH, —$CO_2H$, protected hydroxyl, alkyl, alkenyl, alkynyl, acyl, aryl, heteroaryl, cycloalkyl, heterocycle, —$X_2R^K$, or halides, wherein the alkyl, alkenyl, alkynyl or acyl is optionally substituted with one or more substituents independently selected from the group consisting of halogen, —OH, alkyl, O-alkyl, —$NR^AR^B$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —$N(R^G)$— substituting one or more carbons in the carbon chain, wherein the aryl or heteroaryl, whether alone or as part of a sub stituent group, is optionally substituted with one or more substituents independently selected from the group consisting of halogen, OH, alkyl, O-alkyl, —COOH, —C(O)—$C_{1-4}$ alkyl, —C(O)O—$C_{1-4}$ alkyl, —$NR^CR^D$, —S-alkyl, —SO-alkyl and —$SO_2$-alkyl;

wherein $X_1$ is selected from —O—, —S—, —$SO_2$—, —$N(R^E)$—;

wherein $X_2$ is selected from —O—, —S—, —$SO_2$—, —$N(R^F)$—;

wherein ········· is absent or a $C_{1-3}$ alkylene linker, which links the carbon bonded to $R_9$ and the carbon bonded to $R_{10}$;

wherein $R^A$, $R^B$, $R^C$, $R^D$, $R^E$, $R^F$, $R^K$ and $R^G$ are each independently selected from hydrogen and $C_{1-4}$ alkyl;

4. The process according to any one of paragraphs 1-3, wherein the second compound is (IIA) and $Z_1$ is $CR_2$ or the second compound is (IIB), and $R_2$ in (IIA) and (IIB) is —$CO_2H$, and wherein the process further comprises a decarboxylation step.

5. The process according to paragraph 4, wherein the decarboxylation step comprises continuous flow thermolysis.

6. The process according to any one of the paragraphs 1-5, further comprising diluting the solution comprising CBD or the derivative thereof.

7. The process according to paragraph 6, wherein said diluting produces a two phase solution, having a first and second phase, wherein the first phase has a higher concentration of CBD or the derivative thereof.

8. The process according to paragraph 7, further comprising separating the first phase from the second phase.

9. The process according to paragraph 8, wherein said separating comprises a membrane separation step.

10. The process according to any one of the paragraphs 1-9, further comprising separating CBD or the derivative thereof from the solution comprising the CBD or derivative thereof.

11. The process according to paragraph 10, wherein separating comprises a membrane separation step.

12. The process according to any one of the paragraphs 1-11, further comprising isolating the CBD or derivative thereof using a method selected from crystallization, concentration, distillation, drying, spray drying, precipitation, chromatographic separation, extraction, filtering or combinations thereof.

13. The process according to paragraph 12, wherein said isolating of the CBD or derivative thereof comprises crystallization.

14. The process according to any one of the paragraphs 1-13, wherein the solid acid or heterogeneous acid catalyst is selected from the group consisting of large- and medium-pore zeolites, aluminosilicates, Nafion-NR50, sulfated zirconia, silica gel, polyaniline sulfate, graphene oxide (GO), carboxylic acid-functionalized GO (GO-$CO_2H$), polymer-supported boronic acids, heteropolyacids, tungstated zirconia, heterogeneous sulfonic acids, supported Lewis acid catalysts, protic acids on solid supports, a sulfonic acid-substituted calix[x]arene derivative, β-cyclodextrin, and β-cyclodextrin-derivatives.

15. The process according to paragraph 14, wherein the large- and medium-pore zeolite material is either Zeolite HY or Zeolite Y0.

16. The process according to paragraph 14, wherein the aluminosilicate is Montmorillonite K10 or KSF clay.

17. The process according to paragraph 14, wherein the heterogeneous sulfonic acid is selected from the group consisting of amorphous carbon-bearing supported sulfonic acids, sulfonic acid-functionalized mesoporous silica (SBA-Pr—SO$_3$H), boron sulfonic acid, sulfated tin oxide, and polystyrene-supported sulfonic acid resins.

18. The process according to paragraph 17, wherein the polystyrene-supported sulfonic acid resins is a gel resin.

19. The process according to paragraph 18, wherein the gel resin is Amberlyst-15.

20. The process according to paragraph 18, wherein the polystyrene-supported sulfonic acid resin is a macroporous resin.

21. The process according to paragraph 20, wherein the macroporous resin is macroporous-TsOH (MP-TsOH).

22. The process according to paragraph 14, wherein the supported Lewis acid catalyst is a Lewis acid that is supported on a high-surface-area solid.

23. The process according to paragraph 22, wherein the Lewis acid is selected from the group consisting of AlCl$_3$, BF$_3$, SnCl$_4$, and TiCl$_4$.

24. The process according to paragraph 22, wherein the high-surface-area solid is selected from the group consisting of graphite, Al$_2$O$_3$, MCM-41 SiO$_2$, zeolites, and clays.

25. The process according to paragraph 20, wherein the supported Lewis acid catalyst is chlorinated or fluorinated alumina (Al$_2$O$_3$) or AlCl$_3$ immobilized on mesoporous MCM-41 silica.

26. The process according to claim 14, wherein the β-cyclodextrin-derivative is β-cyclodextrin-butane sulfonic acid, β-cyclodextrin-propyl sulfonic acid, or β-cyclodextrin.

27. The process according to paragraph 14, wherein the β-cyclodextrin-derivative is supported on Dowex resin.

28. The process according to paragraph 14, wherein the calix[x]aren is calix[8]arene sulfonic acid, calix[6]arene sulfonic acid or calix[4]arene sulfonic acid.

29. The process according to paragraph 3, wherein the compound of Formula (IA) is the compound of Formula (IV)

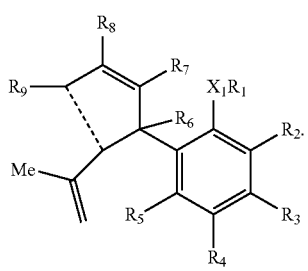

(IV)

30. The process according to paragraph 29, wherein R$_3$ is X$_2$R$^K$.

31. The process according to paragraph 29, wherein R$_3$ is alkyl.

32. The process according to paragraph 29, wherein the compound of Formula (IV) is (−)-cannabidiol (CBD) having the Formula (V)

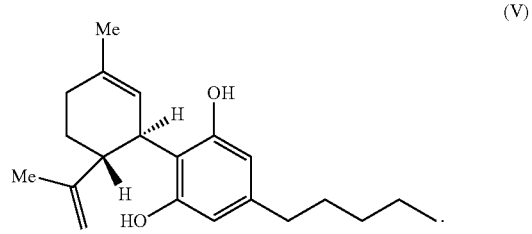 [SMILES: C=C(C)[C@@H]1CCC(C)=C[C@H]1c1c(O)cc(CCCCC)cc1O]

(V)

33. The process according to paragraph 32, wherein the compound of Formula (IV) is the abnormal-CBD, having the formula (V');

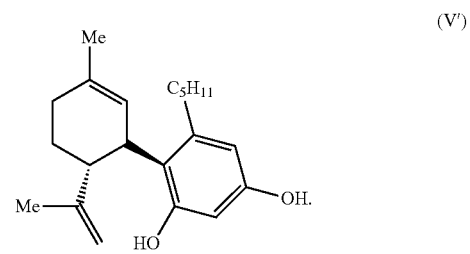

(V')

34. The process according to paragraph 3, wherein the compound of Formula (IA) is the compound of Formula (IV-H$_2$);

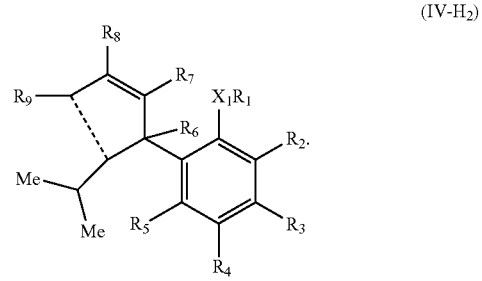

(IV-H$_2$)

35. The process according to paragraph 32, where R$_3$ is X$_2$R$^K$.

36. The process according to paragraph 32, wherein R$_3$ is alkyl.

37. The process according to paragraph 32, wherein the compound of formula (IV-H$_2$) is dihydroCBD (H$_2$CBD) having formula (V-H$_2$);

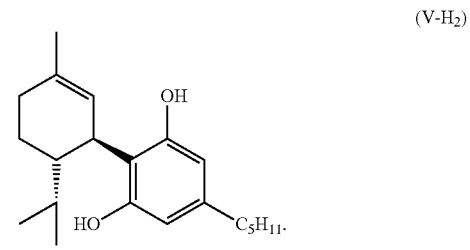

(V-H$_2$)

38. The process according to paragraph 34, wherein the compound of formula (IV-H₂) is abnormal dihydroCBD (abnormal H₂CBD) having formula (V'-H₂);

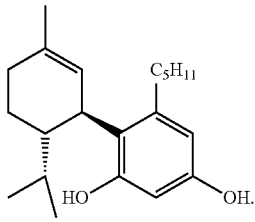

(V'-H₂)

39. The process according to any one of the paragraph 1-38, wherein the compound of Formula (IIA) is olivetol having the structure of Formula (VI), or olivetolic acid having the structure of Formula (VII):

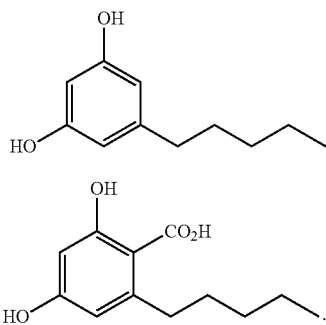

(VI)

(VII)

40. The process according to paragraph 2, wherein the compound of Formula (IIIB) is the compound having the structure (VIII)

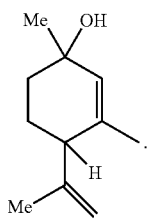

(VIII)

41. The process according to paragraph 40, wherein the compound of Formula (VIII) is (+)-p-mentha-2,8-dien-1-ol having the structure of Formula (IX),

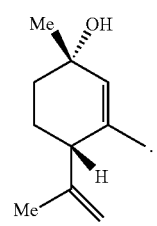

(IX)

42. The process according to paragraph 2, wherein the compound of Formula (IIIC) is α-phellandrene having the structure of Formula (XII);

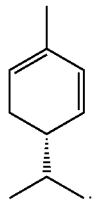

(XII)

43. The process according to paragraph 42, wherein the compound of Formula (XII) is 2-methyl-5-isopropenyl-1,3-cyclohexadiene having the structure of Formula (XIII);

(XIII)

44. A plurality of processes according to any one of paragraphs 1-43, wherein said processes operate in parallel with the process outputs collected synchronously. 45. The process according to any one of paragraphs 1-44, wherein the CBD or derivative thereof is prepared at a scale of greater than 1 kg per day. 46. The process according to any one of paragraphs 1-44, wherein the CBD or derivative thereof is prepared at a scale of greater than 10 kg per day. 47. The process according to any one of paragraphs 1-44, wherein the CBD or derivative thereof is prepared at a scale of greater than 100 kg per day. 48. The process according to any one of paragraphs 1-44, wherein the PBR has an internal volume greater than a cylinder having a diameter of 10 mm and length of 150 mm. 49. The process according to any one of paragraphs 1-44, wherein the PBR has an internal volume greater than or equal to about a cylinder having a diameter of 30 mm and length of 300 mm.

50. The process according to any one of paragraphs 1-44, wherein the compound of Formula (IIA) or (IIB) is selected from a compound in FIG. 1.

51. The process according to any one of paragraphs 1-44, wherein the 1,3-diene is selected from a compound in FIG. 2.

52. The process according to any one of paragraphs 1-44, wherein the allylic alcohol is selected from a compound in FIG. 3.

53. A CBD or derivative thereof made by a process according to any one of paragraphs 1-52. according to any one of the above paragraphs.

54. A CBD or derivative thereof according to paragraph 80 selected from the compounds having structure (IA)-(IF).

55. An automated, scalable, continuous flow reactor system for preparation of CBD or derivative thereof, the system comprising: one or more modular flow chemistry assembly lines; each assembly line comprising (1) controlled input from one or more source pumps for reagents, such as diverse aromatic compounds and oxygenated species or diene species; (2) at least one packed bed reactor (PBR); (3) optionally, at least one heated reactor incorporating one or more membrane separators for waste $CO_2$; (4) optionally, at least one back pressure regulator; (5) optionally, at least one auxiliary pump; (6) optionally, at least one membrane separator for waste water; and (7) one or more collection tanks for the CBD or derivative thereof.

56. The system according to paragraph 55, wherein the at least one packed bed reactor comprises an acid selected from the group consisting of large- and medium-pore zeolites, aluminosilicates, Nafion-NR50, sulfated zirconia, silica gel, polyaniline sulfate, graphene oxide (GO), carboxylic acid functionalized GO (GO-$CO_2$H), polymer-supported boronic acids, heteropolyacids, tungstated zirconia, heterogeneous sulfonic acids, supported Lewis acid catalysts, protic acids on solid supports, a sulfonic acid-substituted calix[x]arene derivative, β-cyclodextrin, and β-cyclodextrin-derivatives.

57. The system according to paragraph 56, wherein the large- and medium-pore zeolite is Zeolite HY or Zeolite Y0.

58. The system according to paragraph 56, wherein the aluminosilicate is Montmorillonite K10 or KSF clay.

59. The system according to paragraph 56, wherein the heterogeneous sulfonic acid is selected from the group consisting of amorphous carbon-bearing supported sulfonic acids, sulfonic acid-functionalized mesoporous silica (SBA-Pr—$SO_3$H), boron sulfonic acid, sulfated tin oxide, and polystyrene-supported sulfonic acid resins.

60. The system according to paragraph 56, wherein the polystyrene-supported sulfonic acid resin is a gel resin.

61. The system according to paragraph 60, wherein the gel resin is Amberlyst-15.

62. The system according to paragraph 60, wherein the polystyrene-supported sulfonic acid resin is a macroporous resin.

63. The system according to paragraph 62, wherein the macroporous resin is macroporous-TsOH (MP-TsOH).

64. The system according to paragraph 56, wherein the supported Lewis acid catalyst is a Lewis acid that is supported on a high-surface-area solid.

65. The system according to paragraph 64, wherein the Lewis acid is selected from the group consisting of $AlCl_3$, $BF_3$, $SnCl_4$, and $TiCl_4$.

66. The system according to paragraph 64, wherein the high-surface-area solid is selected from the group consisting of graphite, $AlCl_2O_3$, MCM-41 $SiO_2$, zeolites, and clays.

67. The system according to paragraph 64, wherein the Lewis acid catalyst is selected from the group consisting of chlorinated or fluorinated alumina ($Al_2O_3$) or $AlCl_3$ immobilized on mesoporous MCM-41 silica.

68. The system according to paragraph 66, wherein the β-cyclodextrin-derivative is β-cyclodextrin-butane sulfonic acid, β-cyclodextrin-propyl sulfonic acid, or β-cyclodextrin.

69. The system according to paragraph 56 or 68, wherein the β-cyclodextrin-derivative is supported on Dowex resin.

70. The system according to paragraph 56, wherein the calix[x]arene is calix[8]arene Sulfonic Acid, calix[6]arene sulfonic Acid or calix[4]arene sulfonic Acid 71. The system according to any one of paragraphs 55-70, wherein the CBD or derivative thereof can be prepared at a scale of greater than 1 kg per day.

72. The system according to any one of paragraphs 55-71, wherein the CBD or derivative thereof can be prepared at a scale of greater than 10 kg per day.

73. The system according to any one of paragraphs 55-72, wherein the CBD or derivative thereof can be prepared at a scale of greater than 100 kg per day.

74. The system according to any one of paragraphs 55-73, wherein the PBR has an internal volume greater than a cylinder having a diameter of 10 mm and length of 150 mm.

75. The system according to any one of paragraphs 55-74, wherein the PBR has an internal volume greater than or equal to about a cylinder having a diameter of 30 mm and length of 300 mm.

76. The system according to any one of paragraphs 55-75, comprising: a modular flow chemistry assembly line comprising (1) controlled input 12 from a first source pump 10 for an aromatic compound and a controlled input 16 from second source pump 14 for oxygenated species or diene species; (2) a packed bed reactor (PBR) 20; (3) a heated reactor 24 incorporating a membrane separator 26 for waste $CO_2$; (4) a back pressure regulator 28; (5) an auxiliary pump 32; (6) a membrane separator for waste water 36; and (7) one or more collection tanks for compound (I).

77. The system according to any one of paragraphs 55-75, comprising: a modular flow chemistry assembly line comprising (1) controlled input 12 from a first source pump 10 for an aromatic compound and controlled input 16 from a second source pump 14 for oxygenated species or diene species; (2) a packed bed reactor (PBR) 20; (3) an auxiliary pump 32; (6) a membrane separator for waste water 36; and (7) one or more collection tanks for compound (I).

78. The system according to any one of paragraphs 55-77, further comprising a separation column prior to the one or more collection tanks.

79. The system according to any one of paragraphs 55-78, wherein the aromatic compound is selected from a compound in FIG. 1.

80. The system according to any one of paragraphs 55-79, wherein the diene species is selected from a compound in FIG. 2.

81. The system according to any one of paragraphs 55-79, wherein the oxygenated species is selected from a compound in FIG. 3

82. A CBD or derivative thereof made by any of the systems according to any one paragraphs 55-81.

83. A CBD or derivative thereof according to paragraph 82 selected from the compounds having structure (IA)-(IF).

The embodiments will be more readily understood by reference to the following examples, which are included merely for purposes of illustration of certain aspects and embodiments of the present invention, and should not be construed as limiting. As such, it will be readily apparent that any of the disclosed specific constructs and experimental plan can be substituted within the scope of the present disclosure.

EXAMPLES

Example 1. Flow-Mediated Synthesis of CBD and Abnormal CBD

To a 20 mL vial are combined olivetol (100 mg, 0.554 mmol) and (5R)-2-methyl-5-(1-methylethenyl)-1,3-cyclohexadiene (81 mg, 0.604 mmol, 1.09 equiv.) in 2-methyl tetrahydrofuran (11 mL). This solution is flowed through an Omnifit EZ Chromatography Column column (6.6 mm bore; total system volume—1.4 mL) filled with MP-TsOH resin beads (600 mg, 1.86 mmol; loading: 3.11 mmol/g) (bed volume=0.75 mL) which is pre-wet with 2-methyl tetrahydrofuran. Using a KD Scientific syringe pump, the reactant solution is added at a rate of 0.06 mL/min. (residence time: 12.5 min). Once reagent flow is completed, a solution of 2-methyl tetrahydrofuran (5 mL) is flowed through the column at 0.06 mL/min in order to elute the remaining reaction solution through the flow system. Solvents are combined and concentrated in vacuo. The crude product is purified by silica gel column chromatography (SiO$_2$; gradient elution hexanes to 55% ethyl ether in hexanes) to afford two isolated products in a total yield of 40% for (−)-CBD and the corresponding abnormal CBD in a 1:1 ratio (35 mg each).

Example 2. Flow-Mediated Synthesis of CBG and Abnormal CBG

In a 20 mL vial is combined olivetol (100 mg, 0.55 mmol) and linalool (93.1 mg, 0.60 mmol, 1.09 equiv) in ethyl acetate (11 mL). This solution is flowed through an Omnifit EZ Chromatography Column (6.6 mm×150 mm; total system volume—1.4 mL) which is filled with MP-TsOH resin beads (600 mg, 1.86 mmol; loading 3.11 mmol/g) (bed volume=0.75 mL) and pre-wet with ethyl acetate. Using a KD Scientific syringe pump, the reactant solution is added at a rate of 0.06 mL/min. (Residence time: 12.5 min) Once reagent flow is completed, a solution of ethyl acetate (5 mL) is flowed through the column at 0.06 mL/min in order to elute the remaining reaction solution through the flow system. The solution is diluted with a pumped aqueous solution (0.1 mL/min) followed by liquid/liquid separation through a membrane separator (Zaiput Flow Technologies). The resulting aqueous solution is collected as waste and the organic solution containing CBG concentrated in vacuo. The crude product is purified by silica gel column (SiO2; gradient elution hexanes to 55% ethyl ether in hexanes) to afford two isolated products in a total yield of 40% for CBG and the corresponding abnormal CBG in a 1:1 ratio (35 mg for each compound).

Example 3. Evaluation of Flow Synthesis Conditions to Produce 8,9-dihydrocannabidiol The reaction of α-phellandrene (XII) and olivetol (VI) to form 8,9-dihydrocannabidiol H$_2$CBD (V-H$_2$) was investigated. The reaction scheme is shown as Scheme 6. Recently, 8,9-dihydrocannabidiol (H$_2$CBD) V-H$_2$ was reported as a non-intoxicating cannabidiol (CBD) derivative for the mitigation of epileptic. Compound V-H$_2$ is an important cannabinoid as it cannot further cyclize to the psychoactive substance tetrahydrocannabinol (THC). The successful implementation of flow chemistry technology to access V-H$_2$ paves the way for application to produce (−)-CBD (V).

Scheme 6

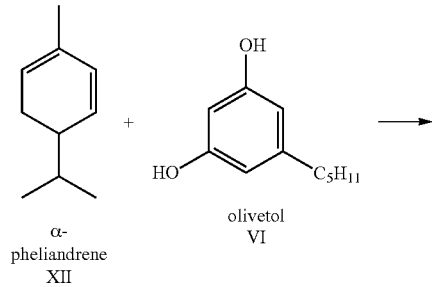

α-pheliandrene
XII olivetol
VI

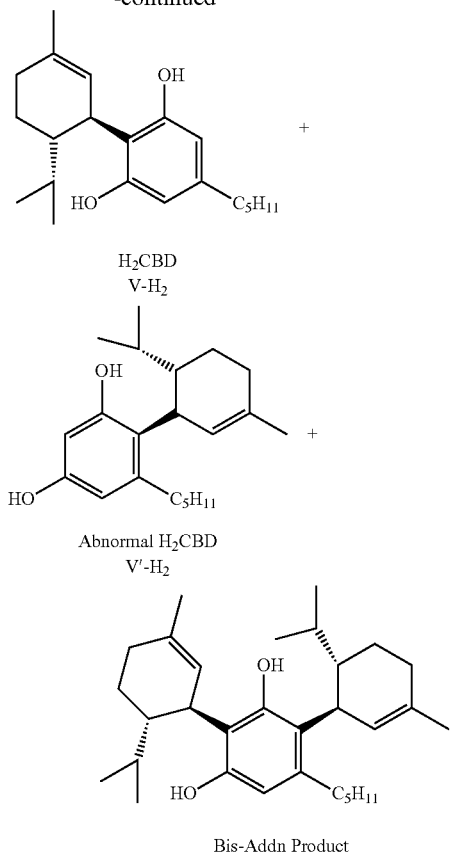

H$_2$CBD
V-H$_2$

Abnormal H$_2$CBD
V'-H$_2$

Bis-Addn Product

Figure 7:
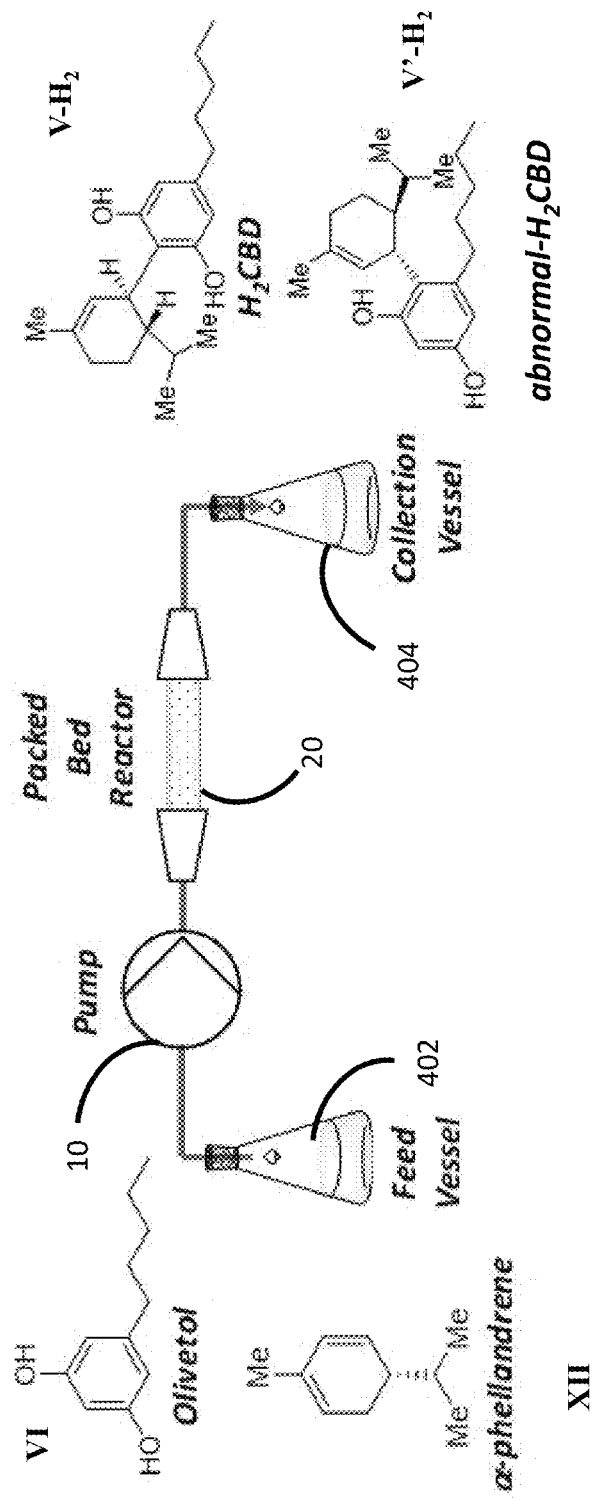
FIG. 7 shows a simple flow reactor design for producing cannabinoids.

Flow synthesis of H$_2$CBD (V-H$_2$) was conducted by employing various solid supported, acid catalysts in a packed bed reactor format. A flow reactor setup was used with a KD Scientific Syringe pump (10) connected via a 1/16 in. OD PTFE tubing assembly to an Omnifit™ EZ Chromatography Column (6.6×150 mm) containing two adjustable endpieces with an inner diameter of 6 mm. To the reactor bed column was added catalyst material in typical amounts of 400 mg per column. A schematic of the flow system used is shown in FIG. 7 where pump 10 is provided to pump olivetol (VI) and a-phellandrene (XII) from feed vessel 402 through the PBR 20. The product H$_2$CBD (V-H$_2$) and abn-H$_2$CBD (V'-H$_2$) are collected into collection vessel 404.

A summary of packed bed reactor (PBR) materials and flow conditions is shown in Table 1. Captisol®, a type of sulfonic acid butyl ether-β-cyclodextrin, was evaluated as a non-supported solid catalyst bed in which case some degree of conversion (35%, Entry 1) to H$_2$CBD (V-H$_2$) and abn-H$_2$CBD (V'-H$_2$) was observed. Succinyl beta-cyclodextrin (Succ-β-CD) similarly produced H$_2$CBD (V-H$_2$) and abn-H$_2$CBD (V'-H$_2$) in poor conversion even with prolonged residence times. The solid acid zeolite Y (780 m$^2$/g) was also evaluated as a catalyst bed. Zeolite Y gave modest yields of H$_2$CBD (V-H$_2$) and s-H$_2$CBD (V'-H$_2$) with ethyl acetate as a solvent, but was found to cake and plug the reactor after repeated use with other solvents such as toluene. Biotage®

MP-TsOH resin (3.11 mmol/g loading), a sulfonated macroporous polystyrene resin, was next evaluated, and very high reactivity was observed with ethyl acetate as solvent (Entry 6). This high degree of reactivity also led to the formation of additional undesired side products (~12%) including bis-addition of α-phellandrene to olivetol, and cyclized (cyclic ether) variants of the dihydroCBD. Based on the results obtained with macroporous tosic acid, a silica-supported tosic acid, $SiO_2$-TsOH (0.68 mmol/g loading, Silicycle), was also evaluated. With this catalyst bed Me-THF was an effective solvent but some retention of material on the silica gel column was observed. Of the various reactor beds evaluated, MP-TsOH resin was determined to be most promising due to the robustness of the system, lack of clogging, ease of loading columns and very high reactivity with ethyl acetate as solvent.

TABLE 1

Evaluation of packed bed materials for efficiency and selectivity of conversion of olivetol + α-phellandrene to $H_2CBD$ and undesired side products.

| Entry | Packed bed material | Solvent | Conc. (M) | Res. time | Percent conversion[a,b] | Product distribution[a,c] $H_2CBD$ | abn-$H_2CBD$ | Other |
|---|---|---|---|---|---|---|---|---|
| 1 | Captisol $SO_3H$ | Me—THF | 0.05 | 10 min | 35% | 33 | 67 | 0 |
| 2 | Succ-βCD | toluene[d] | 0.05 | 35 min | 17% | 38 | 62 | 0 |
| 3 | Succ-βCD | Me—THF | 0.05 | 27.5 min | 33% | 34 | 66 | 0 |
| 4 | Zeolite-Y | EtOAc | 0.05 | 12.5 min | 45% | 40 | 60 | 0 |
| 5 | MP-TsOH | Me—THF | 0.05 | 12.5 min | 10% | 36 | 64 | 0 |
| 6 | MP-TsOH | EtOAc | 0.05 | 12.5 min | 83% | 40 | 48 | 12 |
| 7 | $SiO_2$-TsOH | Me—THF | 0.16 | 15 min | 71% | 55 | 45 | 0 |

[a] Determined by UPLC-MS-ELSD

[b] % conversion determined by olivetol consumption (ELSD);

[c] Observed side products include the bis-addition of α-phellandrene to olivetol, and cyclized (cyclic ether) variants of $H_2CBD$/abn-$H_2CBD$

[d] 3% methanol added to aid solubility. A comprehensive study of solvents, reagent concentrations, and residence times using MP-TsOH resin as packed bed material was conducted to evaluate the influence of these variables on product distribution in flow (Table 2). Use of ethyl acetate (entries 1-4), MBTE (entries 10-11), and acetone (entries 13-14) as solvents generally led to a higher degree of olivetol consumption, but with increased formation of additional undesired side products in small amounts. In contrast, use of methyl THF (MeTHF) led to efficient and cleaner conversion to $H_2CBD$ (V-$H_2$) especially at increased concentration (entries 5-9). Longer residence times (entries 7-9) generally led to improved conversions. Other solvents surveyed, such as MeOH, DMF, toluene, and MeCN (Entries 15-19) all produced significant amounts (>70%) of bis-addition (cf. product 5) and products derived from cycloetherification of $H_2CBD$ (V-$H_2$).

TABLE 2

Effects of solvent, flow rates, and concentration on the efficiency and selectivity of conversion of olivetol and phellandrene to $H_2CBD$ (V-$H_2$), abn-H2CBD (V'-$H_2$) and other side products.

| Entry | Packed bed material | Solvent | Conc. (M) | Res. time | Percent conversion[a,b] | Product distribution[a,c] $H_2CBD$ | abn-$H_2CBD$ | Other |
|---|---|---|---|---|---|---|---|---|
| 1 | MP-TsOH | EtOAc | 0.05 | 6.25 min | 74% | 42 | 55 | 3 |
| 2 | MP-TsOH | EtOAc | 0.05 | 12.5 min | 83% | 40 | 48 | 12 |
| 3 | MP-TsOH | EtOAc | 0.08 | 16 min | 59% | 51 | 40 | 9 |
| 4 | MP-TsOH | EtOAc | 0.16 | 12.5 min | 60% | 50 | 43 | 7 |
| 5 | MP-TsOH | Me-THF | 0.05 | 12.5 min | 10% | 36 | 64 | 0 |
| 6 | MP-TsOH | Me-THF | 0.16 | 10 min | 19% | 43 | 57 | 0 |
| 7 | MP-TsOH | Me-THF | 0.16 | 12.5 min | 82% | 53 | 41 | 6 |
| 8 | MP-TsOH | Me-THF | 0.16 | 16.7 min | 72% | 45 | 55 | 0 |
| 9 | MP-TsOH | Me-THF | 0.16 | 25 min | 59% | 44 | 56 | 0 |
| 10 | MP-TsOH | MTBE | 0.05 | 7.3 min | 23% | 35 | 65 | 0 |
| 11 | MP-TsOH | MTBE | 0.16 | 16.6 min | 95% | 38 | 42 | 20 |
| 13 | MP-TsOH | Acetone | 0.05 | 6.25 min | 75% | 41 | 53 | 6 |
| 14 | MP-TsOH | Acetone | 0.05 | 12.5 min | 53% | 43 | 54 | 4 |
| 15 | MP-TsOH | MeOH | 0.08 | 6.3 min | 70% | 49 | 51 | 0 |
| 16 | MP-TsOH | MeOH | 0.08 | 12.5 min | 100% | <10% | 0 | >90% |
| 17 | MP-TsOH | DMF | 0.08 | 12.5 min | 37% | 0 | 0 | 100 |
| 12 | MP-TsOH | Toluene | 0.16 | 12.5 min | 100% | 11 | 0 | 89 |
| 18 | MP-TsOH | MeCN | 0.05 | 5.5 min | 75% | 16 | 10 | 74 |
| 19 | MP-TsOH | MeCN | 0.05 | 11 min | 76% | 0 | 7 | 93 |

[a] Determined by UPLC-MS-ELSD

[b] % conversion determined by olivetol consumption (ELSD);

[c] Observed side products include bis-addition of α-phellandrene to olivetol, and cyclized variants of $H_2CBD$/abn-$H_2CBD$.

Example 4: Experimental Procedure For Flow-Mediated Production of 8,9-Dihydrocannabidiol (H₂CBD)

To a two-dram vial was combined olivetol (30 mg, 166.4 μmol) and α-phellandrene (24.7 mg, 181.42 μmol) in ethyl acetate (3 mL). This solution was flowed through an Omnifit EZ Chromatography Column (6.6 mm bore; total system volume—1.4 mL) filled with MP-TsOH (402 mg, 166.44 μmol; loading: 3.11 mmol/g) (bed volume: 0.5 mL) which is pre-wet with ethyl acetate. Using a KD Scientific syringe pump, the reactant solution was added at a rate of 0.04 mL/min. (residence time: 12.5 min). Once reagent flow was completed, a solution of ethyl acetate (4 mL) was flowed through the column at 0.04 mL/min in order to elute the remaining reaction solution through the system. Solvents were combined and concentrated in vacuo. The crude product was purified by silica gel column chromatography (SiO₂, gradient elution hexanes to 55% ethyl ether in hexanes) to afford two isolated products.

¹H NMR (400 MHz, CDCl₃) δ 5.98-6.37 (br m, 2H), 5.53 (br s, 1H), 4.57 (br s, 1H), 3.81 (br d, J=8.6 Hz, 1H), 2.46 (t, J=7.82, 2H), 2.03-2.25 (br t, 2H), 1.81 (m, 1H), 1.78 (s, 3H), 1.50-1.70 (m, 5H), 1.17-1.49 (m, 5H), 0.81-0.97 (m, 9H).

UPC2 (Viriis BEH column, 1-10% MeOH/CO2): M+H 317, RT=1.95 min.

(3S,4R)-8,9-Dihydro-o-cannabidiol, abnormal H₂CBD: 11 mg (21%)

¹H NMR (400 MHz, CDCl₃) δ 6.24 (d, J=2.45 Hz, 1H), 6.22 (d, J=2.45 Hz, 1H), 6.07 (s, 1H), 5.48 (br s, 1H), 4.53-4.85 (br s, 1H), 3.44 (br d, J=9.4 Hz, 1H), 2.61-2.73 (m, 1H), 2.30-2.41 (m, 1H), 2.13 (m, 2H), 1.78 (s, 6H), 1.52 (br s, 2H), 1.33 (br s, 4H), 1.26 (s, 2H), 0.91 (br t, J=6.64 and 6.25 Hz, 3H), 0.84 (t, J=6.4 Hz, 6H). UPC2 (Viriis BEH column, 1-10% MeOH/CO2): M+H 317, RT=2.64 min.

Example 5: Application to the Flow-Mediated Synthesis of (−)-CBD

Based on the successful flow-mediated synthesis of H₂CBD (V-H₂), a smooth application to the flow-mediated synthesis of (−)-CBD (Scheme 7) is expected. For the case of CBD (V), the requisite reaction partner 2-methyl-5-isopropenyl-1,3-cyclohexadiene (XIII) was prepared as shown in Scheme 7(a) from (R)-(−)-carvone. The methodology involves preparation of the intermediate tosylhydrazone of (R)-(−)-carvone followed by Shapiro reaction with methyllithium. This is a general method to produce various conjugated dienes from α,β-unsaturated ketones and alkyllithium reagents as possible reaction partners for flow-mediated synthesis of cannabinoids. Compound XIII can be used in flow-mediated synthesis with olivetol (cf. Scheme 7 (b)) to produce (−)-CBD (V) or its abnormal CBD isomer (V'). Based on our solvent study (cf. Table 2, entries 8-9), use of Me-THF as solvent in particular should suppress cycloetherification of (−)-CBD V to tetrahydrocannabinol (THC) which is generally observed under strongly acidic conditions.

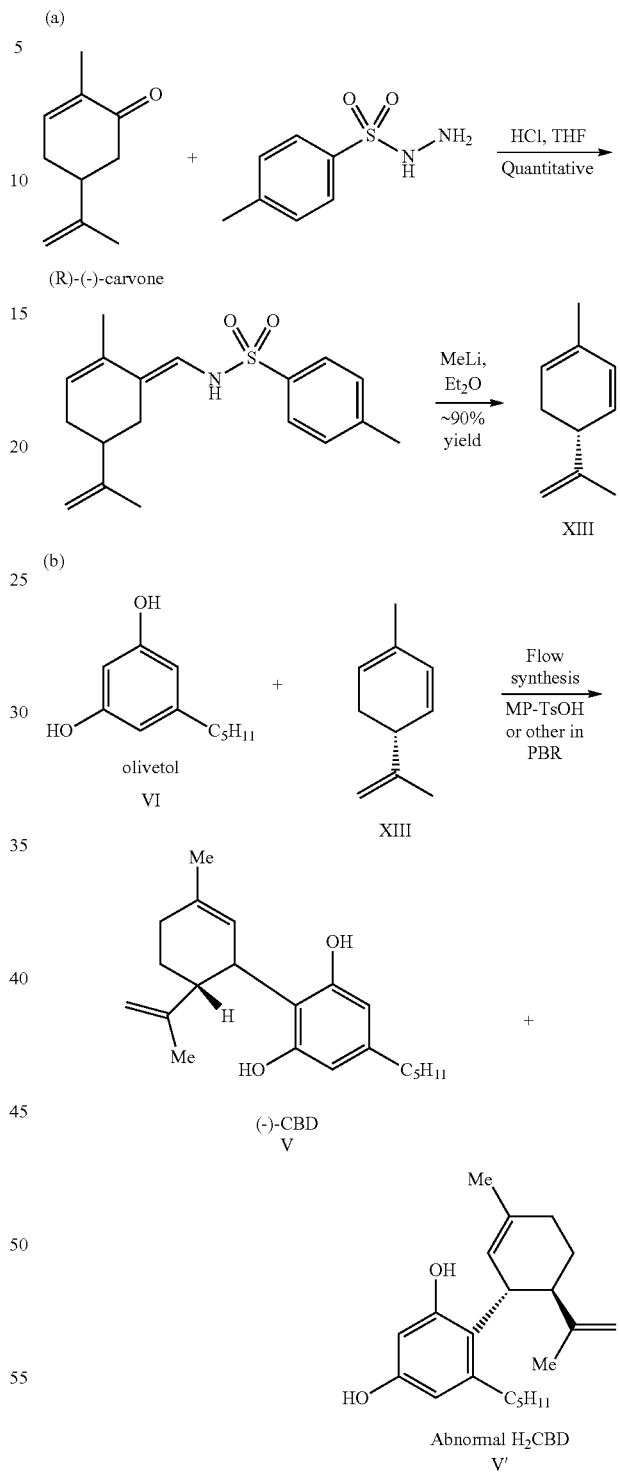

Scheme 7

Example 6. Formulation of a Solid Oral Dosage Form

An oral composition including 100 mg, 250 mg, and 500 mg of compounds prepared as in any of the Examples 1-5 is formulated with sufficient finely divided lactose to provide a total amount of material, 580 to 590 mg, to fill an O-sized hard gel capsule.

REFERENCES

Phytocannabinoids: a unified critical inventory. Lumir Ondrej Hanus, Stefan Martin Meyer, Eduardo Munoz, Orazio Taglialatela-Scafati and Giovanni Appendino. Nat. Prod. Rep., 2016, 33, 1357-1392.

Antibacterial Cannabinoids from *Cannabis sativa*: A Structure-Activity Study. Giovanni Appendino, Simon Gibbons, Anna Giana, Alberto Pagani, Gianpaolo Grassi, Michael Stavri, Eileen Smith, M. Mukhlesur Rahman J. Nat. Prod. 2008, 71, 1427-1430

Ben-Shabat S., Hanus L. O., Katzavian G., Gallily R. New cannabidiol derivatives: synthesis, binding to cannabinoid receptor, and evaluation of their antiinflammatory activity. *J Med Chem.* 2006; 49(3):1113-7.

Mascal M., Hafezi N., Wang D., Hu Y., Serra G., Dallas M. L., Spencer J. P. E. Synthetic, non-intoxicating 8,9-dihydrocannabidiol for the mitigation of seizures. *Sci Rep.* 2019; 9(1):7778. PMCID: PMC6533278.

Ran Y., Li M., Zhang Z. Z. beta-Cyclodextrin-Propyl Sulfonic Acid Catalysed One-Pot Synthesis of 1,2,4,5-Tetrasubstituted Imidazoles as Local Anesthetic Agents. *Molecules.* 2015; 20(11):20286-96. PMCID: PMC6332507.

Shinde V. V., Jung S. Succinyl-β-cyclodextrin-driven synthesis of a nitrogen-fused five-ring heterocycle using GBB-based [4+1] cycloaddition via supramolecular host-guest interactions. *Tetrahedron.* 2019; 75(6):778-83.

Liu F., Huang K., Zheng A., Xiao F.-S., Dai S. Hydrophobic Solid Acids and Their Catalytic Applications in Green and Sustainable Chemistry. *ACS Catalysis.* 2018; 8(1):372-91.

Crombie L., Crombie W. M. L., Firth D. F. Terpenylations using (R)-(−)-α-phellandrene. Synthesis of the (3 S,4R)-8,9-dihydro-o- and -p-cannabidiols, their iso-THC's, and the natural dihydrochalcone (3 S,4R)-(+)-linderatin. *Journal of the Chemical Society, Perkin Transactions 1.* 1988 (5): 1251-3.

Dauben W. G., Lorber M. E., Vietmeyer N. D., Shapiro R. H., Duncan J. H., Tomer K. Tosylhydrazones. VIII. Preparation of conjugated dienes from tosylhydrazones of .alpha.,.beta.-unsaturated ketones and alkyllithium reagents. *Journal of the American Chemical Society.* 1968; 90(17):4762-3.

Razdan R. K., Dalzell H. C., Handrick G. R. Hashish. A simple one-step synthesis of (−)-delta1-tetrahydrocannabinol (THC) from p-mentha-2,8-dien-1-ol and olivetol. *J Am Chem Soc.* 1974; 96(18):5860-5.

Chakraborit et al., "Protic Acid Immobilized on Solid Support as an Extremely Efficient Recyclable Catalyst System for a Direct and Atom Economical Esterification of Carboxylic Acids With Alcohols" J. Org. Chem., (2009) 74 (16), 5967-74.

An L et al., "Calix[8]arene Sulfonic Acid Catalyzed Three-Component Reaction for Convenient Synthesis of 3,4-Dihydropyrimidin-2(1H)-ones/thiones under Ultrasonic Irradiation", Biol Pharm Bull, (2016); 39(2):267-71.

Da Silva D L et al., "Xanthenones: calixarenes-catalyzed syntheses, anticancer activity and QSAR studies", *Org. Biomol. Chem.* (2015) Mar. 21; 13(11):3280-7.

As used herein the term "comprising" or "comprises" is used in reference to compositions, methods, and respective component(s) thereof, that are essential to the claimed invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the claimed invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A process for the preparation of a cannabidiol (CBD) or a derivative thereof, the process comprising:
   (a) providing a solution comprising of a first compound that is a 1,3-diene, an allylic alcohol or an allylic ether and a second compound of Formula (IIA) or (IIB) into a packed-bed reactor (PBR) comprising a solid or heterogeneous catalyst;
   (b) circulating the first and second compound through the PBR to react the first compound with the second compound;
   (c) collecting from the PBR a solution comprising the CBD or a derivative thereof;
   wherein the structures of (IIA) and (IIB) are:

(IIA)

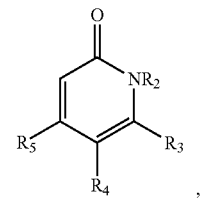

(IIB)

wherein: $Z_1$ is $CR_2$ or N;

$Z_2$ is $CR_4$ or N;

wherein $R_1$, $R_3$, $R_5$, are each independently selected from the group consisting of H, OH, —$CO_2H$, protected hydroxyl, alkyl, alkenyl, alkynyl, acyl, aryl, heteroaryl, cycloalkyl, heterocycle, —$X_2R^K$, or halides, wherein $R_2$, and $R_4$, are each independently selected from the group consisting of H, OH, —$CO_2H$, protected hydroxyl, alkyl, alkenyl, alkynyl, acyl, aryl, heteroaryl, cycloalkyl, heterocycle, —$X_2R^K$ and not selected from halides, wherein the alkyl, alkenyl, alkynyl or acyl is optionally substituted with one or more substituents independently selected from the group consisting of halogen, —OH, alkyl, O-alkyl, —$NR^AR^B$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —$N(R^G)$— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —COOH, —C(O)—$C_{1-4}$ alkyl, —C(O)O—$C_{1-4}$ alkyl, —$NR^CR^D$, —S-alkyl, —SO-alkyl and —$SO_2$-alkyl;

wherein $X_1$ is selected from —O—, —S—, —$SO_2$—, —$N(R^E)$—;

wherein $X_2$ is selected from —O—, —S—, —$SO_2$—, —$N(R^F)$—;

wherein $R^A$, $R^B$, $R^C$, $R^D$, $R^E$, $R^F$, $R^K$ $R^G$ are each independently selected from hydrogen and $C_{1-4}$ alkyl;

or a pharmaceutically acceptable salt or ester thereof.

2. The process according to claim 1, wherein the first compound has a structure selected from the group consisting of:

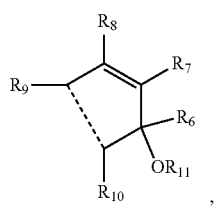

(IIIA)

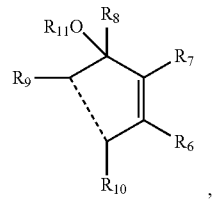

(IIIB)

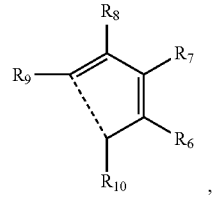

(IIIC)

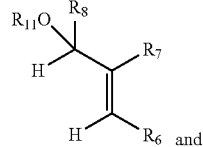

(IIID)

and

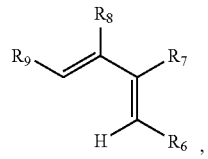

(IIIE)

wherein $R_6$, $R_7$, $R_8$, $R_9$, $R_{10}$ and $R_{11}$ are each independently selected from the group consisting of H, OH, —$CO_2H$, protected hydroxyl, alkyl, alkenyl, alkynyl, acyl, aryl, heteroaryl, cycloalkyl, heterocycle, —$X_2R^K$, or halides, wherein the alkyl, alkenyl, alkynyl or acyl is optionally substituted with one or more substituents independently selected from the group consisting of halogen, —OH, alkyl, O-alkyl, —$NR^AR^B$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —$N(R^G)$— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —COOH, —C(O)—$C_{1-4}$ alkyl, —C(O)O—$C_{1-4}$ alkyl, —$NR^CR^D$, —S-alkyl, —SO-alkyl and —$SO_2$-alkyl;

wherein $X_1$ is selected from —O—, —S—, —$SO_2$—, —$N(R^E)$—;

wherein $X_2$ is selected from —O—, —S—, —$SO_2$—, —$N(R^F)$—;

wherein ------ is absent or a $C_{1-3}$ alkylene linker, which links the carbon bonded to $R_9$ and the carbon bonded to $R_{10}$;

wherein $R^A$, $R^B$, $R^C$, $R^D$, $R^E$, $R^F$, $R^K$, and $R^G$ are each independently selected from hydrogen and $C_{1-4}$ alkyl;

or a pharmaceutically acceptable salt or ester thereof.

3. The process of claim 1, wherein the CBD or the derivative thereof has a structure selected from the group consisting of:

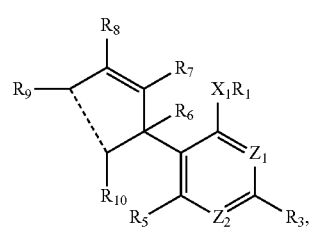

(IA)

-continued

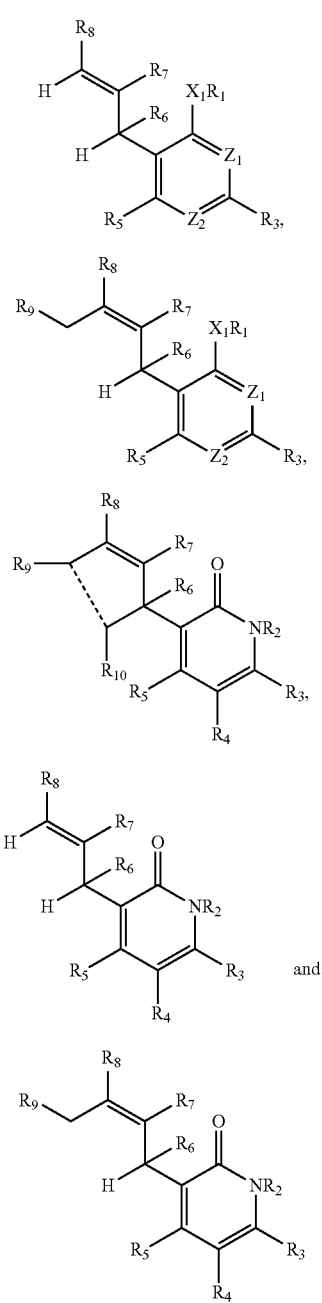

wherein $R_6$, $R_7$, $R_8$, $R_9$, and $R_{10}$ are each independently selected from the group consisting of H, OH, —$CO_2H$, protected hydroxyl, alkyl, alkenyl, alkynyl, acyl, aryl, heteroaryl, cycloalkyl, heterocycle, —$X_2R^K$, or halides, wherein the alkyl, alkenyl, alkynyl or acyl is optionally substituted with one or more substituents independently selected from the group consisting of halogen, —OH, alkyl, O— alkyl, —$NR^AR^B$, —S-alkyl, —SO-alkyl, —$SO_2$-alkyl, alkenyl, alkynyl, aryl, heteroaryl, cycloalkyl or heterocycle;

wherein the aryl or heteroaryl, whether alone or as part of a substituent group, is optionally substituted with one or more substituents independently selected from the group consisting of halogen, OH, alkyl, O-alkyl, —COOH, —C(O)—$C_{1-4}$ alkyl, —C(O)O—$C_{1-4}$ alkyl, —$NR^CR^D$, —S-alkyl, —SO-alkyl and —$SO_2$-alkyl;

wherein $X_1$ is selected from —O—, —S—, —$SO_2$—, —N($R^E$)—;

wherein $X_2$ is selected from —O—, —S—, —$SO_2$—, —N($R^F$)—;

wherein ----- is absent or a $C_{1-3}$ alkylene linker, which links the carbon bonded to $R_9$ and the carbon bonded to $R_{10}$;

wherein $R^A$, $R^B$, $R^C$, $R^D$, $R^E$, $R^F$ and $R^K$ are each independently selected from hydrogen and $C_{1-4}$ alkyl.

4. The process according to claim 1, wherein the second compound is (IIA) and $Z_1$ is $CR_2$ or the second compound is (IIB), and $R_2$ in (IIA) and (IIB) is —$CO_2H$, and wherein the process further comprises a decarboxylation step.

5. The process according to claim 4, wherein the decarboxylation step comprises continuous flow thermolysis.

6. The process according to claim 1, further comprising diluting the solution comprising CBD or the derivative thereof.

7. The process according to claim 6, wherein said diluting produces a two phase solution, having a first and second phase, wherein the first phase has a higher concentration of CBD or the derivative thereof.

8. The process according to claim 7, further comprising separating the first phase from the second phase.

9. The process according to claim 8, wherein said separating comprises a membrane separation step.

10. The process according to claim 1, further comprising separating CBD or the derivative thereof from the solution comprising the CBD or derivative thereof.

11. The process according to claim 10, wherein separating comprises a membrane separation step.

12. The process according to claim 1, further comprising isolating the CBD or derivative thereof using a method selected from crystallization, concentration, distillation, drying, spray drying, precipitation, chromatographic separation, extraction, filtering or combinations thereof.

13. The process according to claim 3, wherein the compound of Formula (IA) is the compound of Formula (IV)

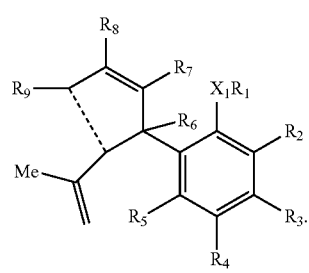

14. The process according to claim 13, wherein $R_3$ is $X_2R^K$.

15. The process according to claim 13, wherein $R_3$ is alkyl.

16. The process according to claim 13, wherein the compound of Formula (IV) is (−)-cannabidiol (CBD) having the Formula (V)

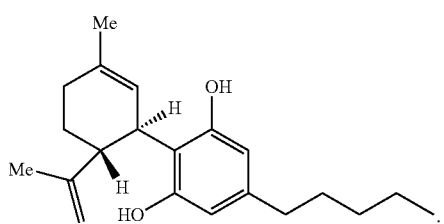

(V)

17. The process according to claim 16, wherein the compound of Formula (IV) is the abnormal-CBD, having the formula (V');

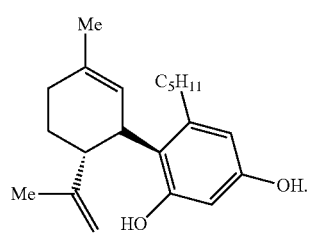

(V')

18. The process according to claim 3, wherein the compound of Formula (IA) is the compound of Formula (IV-$H_2$);

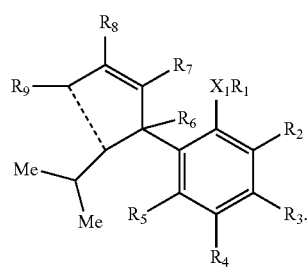

(IV-$H_2$)

19. The process according to claim 18, where $R_3$ is $X_2R^K$.

20. The process according to claim 18, wherein $R_3$ is alkyl.

21. The process according to claim 18, wherein the compound of formula (IV-$H_2$) is hydrogenated CBD ($H_2$CBD) having formula (V-$H_2$);

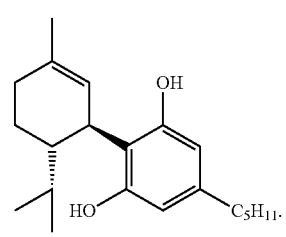

(V-$H_2$)

22. The process according to claim 18, wherein the compound of formula (IV-$H_2$) is abnormal hydrogenated CBD (Abnormal $H_2$CBD) having formula (V'-$H_2$);

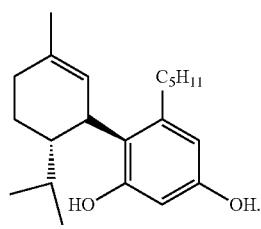

(V'-$H_2$)

23. The process according to claim 1, wherein the compound of Formula (IIA) is olivetol having the structure of Formula (VI), or olivetolic acid having the structure of Formula (VII):

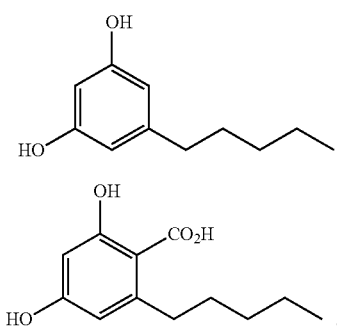

(VI)

(VII)

24. The process according to claim 2, wherein the compound of Formula (IIIB) is the compound having the structure (VIII)

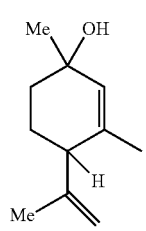

(VIII)

25. The process according to claim 24, wherein the compound of Formula (VIII) is (+)-p-mentha-2,8-dien-1-ol having the structure of Formula (IX),

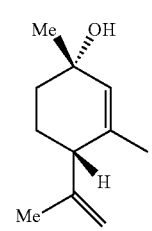

(IX)

26. The process according to claim 2, wherein the compound of Formula (IIC) is α-phellandrene having the structure of Formula (XII);

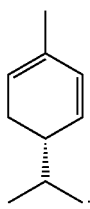

(XII)

27. The process according to claim 24, wherein the compound of Formula (XII) is 2-methyl-5-isopropenyl-1,3-cyclohexadiene having the structure of Formula (XIII);

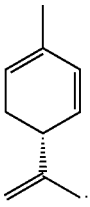

(XIII)

28. A plurality of processes according to claim 1, wherein said processes operate in parallel with the process outputs collected synchronously.

29. An automated, scalable, continuous flow reactor system for preparation of CBD or derivative thereof, the system comprising: one or more modular flow chemistry assembly lines; each assembly line comprising (1) controlled input from one or more source pumps for reagents; (2) at least one packed bed reactor (PBR); (3) optionally, at least one heated reactor incorporating one or more membrane separators for waste $CO_2$; (4) optionally, at least one back pressure regulator; (5) optionally, at least one auxiliary pump; (6) optionally, at least one membrane separator for waste water; and (7) one or more collection tanks for the CBD or derivative thereof.

30. The system according to claim 29, wherein the at least one packed bed reactor comprises an acid selected from the group consisting of large- and medium-pore zeolites, aluminosilicates, sulfonated tetrafluoroethylene fluoropolymer-copolymer, sulfated zirconia, silica gel, polyaniline sulfate, graphene oxide (GO), carboxylic acid functionalized GO (GO-$CO_2$H), polymer-supported boronic acids, heteropolyacids, tungstated zirconia, heterogeneous sulfonic acids, supported $AlCl_3$, supported $SnCl_4$, supported $TiCl_4$, protic acids on solid supports, a sulfonic acid-substituted calix[x]arene derivative, β-cyclodextrin, and β-cyclodextrin-derivatives.

* * * * *